United States Patent
Isab et al.

(10) Patent No.: US 11,142,539 B2
(45) Date of Patent: Oct. 12, 2021

(54) PHOSPHINOGOLD(I) COMPLEXES AND METHODS OF TREATING CANCER

(71) Applicant: King Fahd University of Petroleum and Minerals, Dhahran (SA)

(72) Inventors: Anvarhusein A. Isab, Dhahran (SA); Adam Ahmed Abdullah Sulaiman, Dhahran (SA); Ali Alhoshani, Dhahran (SA)

(73) Assignees: King Fahd University of Petroleum and Minerals, Dhahran (SA); King Saud University, Riyadh (SA)

( * ) Notice: Subject to any disclaimer, the term of this patent is extended or adjusted under 35 U.S.C. 154(b) by 0 days.

(21) Appl. No.: 16/814,489

(22) Filed: Mar. 10, 2020

(65) Prior Publication Data
US 2021/0284674 A1 Sep. 16, 2021

(51) Int. Cl.
*C07F 19/00* (2006.01)
*A61P 35/00* (2006.01)

(52) U.S. Cl.
CPC ............ *C07F 19/005* (2013.01); *A61P 35/00* (2018.01)

(58) Field of Classification Search
CPC .............................. A61P 35/00; C07F 19/005
See application file for complete search history.

(56) References Cited

U.S. PATENT DOCUMENTS

| 2015/0266909 A1 | 9/2015 | Isab et al. |
| 2017/0197997 A1 | 7/2017 | Altaf et al. |
| 2017/0305942 A1 | 10/2017 | Al-Jaroudi et al. |

FOREIGN PATENT DOCUMENTS

WO 2018/069525 A1 4/2018

OTHER PUBLICATIONS

Chen, et al. ; In vitro antibacterial and time kill evaluation of mononuclear phosphanegold(I) dithiocarbamates ; Journal of Inorganic Biochemistry, vol. 163 ; pp. 68-80 ; Oct. 2016 ; Abstract Only ; 3 Pages.

Altaf, et al. ; Synthesis, characterization and anticancer activity of gold(I) complexes that contain tri-tert-butylphosphine and dialkyl dithiocarbamate ligands ; European Journal of Medicinal Chemistry, vol. 95 ; pp. 464-472 ; May 5, 2015 ; Abstract Only ; 3 Pages.

Altaf, et al. ; The synthesis, spectroscopic characterization and anticancer activity of new mono and binuclear phosphanegold(I) dithiocarbamate complexes† ; New Journal of Chemistry, Issue 1 ; 2015 ; Abstract Only ; 6 Pages.

Jamaludin, et al. ; Phosphanegold(I) dithiocarbamates, R PAu[Sc(S)N(Pr)CH CH OH] for R = Ph, Cy and Et: Role of phosphanebound R substituents upon in vitro cytotoxicity against MCF-7R breast cancer cells and cell death pathways ; European Journal of Medicinal Chemistry, vol. 67 ; pp. 127-141 ; Sep. 2013 ; Abstract Only ; 3 Pages.

Gandin, et al. ; Cancer cell death induced by phosphine gold(I) compounds targeting thioredoxin reductase ; Biochemical Parhmacology, vol. 79, Issue 2 ; pp. 901-101 ; Jan. 15, 2010 ; Abstract Only ; 3 Pages.

Ho, et al. ; (N,N-Di ethyl di thio carbamato)(tri cyclo hexyl phosphine)-gold(I) ; Crystallographic Communications, vol. 57, Part 12 ; Dec. 2001 ; Abstract Only ; 5 Pages.

Faamau, et al. ; Characterization of [μ-Bis(Diphenylphosphino)Alkane] Bis[N,Ndialkyldithiocarbamato) Gold(I)] Complexes: X-Ray Crystal Structure of [(Ph 2P(CH2)2PPh2)(AuS2CNEt2)2] ; Journal of Coordination Chemistry, vol. 31, Issue 2 ; Sep. 23, 2006 ; Abstract Only ; 4 Pages.

Mirabelli, et al. ; Antitumor activity of bis(diphenylphosphino)alkanes, their gold(I) coordination complexes, and related compounds ; J. Med. Chem. 30, 12 ; pp. 2181-2190 ; Dec. 1, 1987 ; 15 Pages.

*Primary Examiner* — Matthew P Coughlin
*Assistant Examiner* — Thurman Wheeler
(74) *Attorney, Agent, or Firm* — Oblon, McClelland, Maier & Neustadt, L.L.P.

(57) ABSTRACT

Mixed ligand phosphinogold(I) complexes as anticancer agents. The gold(I) ion of the complexes is coordinated to a phosphine and a dithiocarbamate or halogen ligand. Also described are a pharmaceutical composition incorporating the phosphinogold(I) complex, a method of synthesizing the phosphinogold(I) complex, and a method of treating cancer. The phosphinogold(I) complexes exhibit potent cytotoxicity against lung, cervical, and liver cancer cells.

20 Claims, 4 Drawing Sheets

1

2

3

4

PHOSPHINOGOLD(I) COMPLEXES AND METHODS OF TREATING CANCER

STATEMENT OF ACKNOWLEDGEMENT

This research was supported by King Fand University of Petroleum and Minerals under the project number IN171005.

BACKGROUND OF THE INVENTION

Technical Field

The present disclosure relates to phosphinogold(I) dithiocarbamate-containing complexes and phosphinogold(I) halogen-containing complexes with anti-proliferative properties, and pharmaceutical compositions and uses thereof.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Gold(I) complexes have played an important role in the treatment of rheumatoid arthritis for many years [L. Messori and G, Marcon Met Ions Biol Syst., 41 (2004) 279-304; C. F. Shaw III, Chem. Rev. 99 (1999) 2589-2600; L. R. A. James, Z.-Q. Xu, R. Sluyter, E. L. Hawksworth, C. Kelso, B. Lai, D. J. Paterson, M. D. de Jonge, N. E. Dixon, J. L. Beck, S. F. Ralph, C. T. Dillon, J. Inorg. Biochem. 142 (2015) 28-38; I. Ott, Coord. Chem. Rev. 253 (2009) 1670-1681; and S. J. Berners-Price, A. Filipovska, Metallomics 3 (2011) 863-873]. Later, it was found that the patients receiving chrysotherapy for arthritis exhibited lower evidence of malignancy rates and thus, it was suggested that gold complexes might demonstrate antitumor properties [Fries, J. F.; Bloch, D.; Spitz, P.; Mitchell, D. M. Am. J. Med. (1985), 78, 56-59; and Ward, J. R. Am. J. Med. 1988, 85, 39-44, each incorporated herein by reference in their entirety]. For example, the orally active anti-arthritis drug auranofin [T. M. Simon, D. H. Kunishima, G. J. Vibert, A. Lorber, Cancer Res. 41 (1981) 94; C. K. Mirabelli, R. K. Johnson, C. M. Sung, L. Faucette, K. Muirhead, S. T. Crooke, Cancer Res. 1985, 45, 32-39; and C. Marzano, V. Gandin, A. Folda, G. Scutari, A. Bindoli, M. P. Rigobello, Free Radical Biology & Medicine 42 (2007) 872-881, each incorporated herein by reference in their entirety] and tetrahedral gold(I) complexes containing disphosphane ligands [S. J. Berners-Price, C. K. Mirabelli, R. K. Johnson, M. R. Mattern, F. L. McCabe, L. F. Faucette, C.-M. Sung, S.-M. Mong, P. J. Sadler, S. T. Crooke, Cancer Res. 46 (1986) 5486; Peter C. Healy, Bradley T. Loughrey, Michael L. Williams, Peter G. Parsons, J. Inorg. Biochem. 104 (2010) 625-631; and G. Lupidi, L. Avenali, M. Bramucci, L. Quassinti, R. Pettinari, H. K. Khalife, H. Gali-Muhtasib, F. Marchetti, C. Pettinari, J. Inorg. Biochem. 124 (2013) 78-87, each incorporated herein by reference in their entirety], particularly [Au(dppe)$_2$]Cl (dppe=1,2-bis(diphenylphosphano)ethane) [S. J. Berners-Price, C. K. Mirabelli, R. K. Johnson, M. R. Mattern, F. L. McCabe, L. F. Faucette, C.-M. Sung, S.-M. Mong, P. J. Sadler, S. T. Crooke, Cancer Res. 46 (1986) 5486, incorporated herein by reference in its entirety] were found to possess potent anticancer activity against a range of tumor models in mice, including ovarian cancer cells and a cisplatin-resistant subline of P388 leukemia. Therefore, cytotoxic properties of other gold(I) complexes containing phosphane and thiolate ligands have been investigated [S. Nobili, E. Mini, I. Landini, C. Gabbiani, A. Casini, L. Messori, Med. Res. Rev. 105 (2010) 550-580; Tiekink, E. R. T.; Inflammopharmacology 2008, 16, 138; Tiekink, E. R. T. Bioinorg. Chem. Appl. 2003, 1, 53; C. K. Mirabelli, R. K. Johnson, D. T. Hill, L. F. Faucette, G. R. Girard, G. Y. Kuo, C. M. Sung, S. T. Crooke, J. Med. Chem. 1986, 29, 218-223; Marzo, T.; Cirri, D.; Gabbiani, C.; Gamberi, T.; Magherini, F.; Pratesi, A.; Guerri, A.; Biver, T.; Binacchi, F.; Stefanini, M.; Arcangeli, A.; ACS Med. Chem. Lett. 2017, 8, 997-1001; T. Marzo, L. Massai, A. Pratesi, M. Stefanini, D. Cirri, F. Magherini, M. Becatti, I. Landini, S. Nobili, E. Mini, O. Crociani, A. Arcangeli, S. Pillozzi, T. Gamberi, L. Messori, ACS Med. Chem. Lett. 10 (2019) 656-660; F. K. Keter, I. A. Guzei, M. Nell, W. E. van Zyl, J. Darkwa, Inorg. Chem. 2014, 53, 2058-2067; M. Serratrice, M. A. Cinellu, L. Maiore, M. Pilo, A. Zucca, C. Gabbiani, A. Guerri, I. Landini, S. Nobili, E. Mini, L. Messori, Inorg. Chem. 2012, 51, 3161-3171; J. D. S. Chaves, F. Neumann, T. M. Francisco, C. C. Corrêa, M. T. P. Lopes, H. Silva, A. P. S. Fontes, and M. V. de Almeida, Inorg. Chim. Acta 414 (2014) 85-90; K. K. Ooi, C. I. Yeo, K.-P. Ang, A. M. Akim, Y.-K. Cheah, S. N. A. Halim, H.-L. Seng, and E. R. T. Tiekink, J. Biol. Inorg. Chem., 20 (2015) 855-873; M. P. Chrysouli, C. N. Banti, N. Kourkoumelis, N. Panayiotou, G. S. Markopoulos, A. J. Tasiopoulos, S. K. Hadjikakou, J. Inorg. Biochem. 179 (2018) 107-120; C. K. Adokoh, J. Darkwa, H. H. Kinfe, Polyhedron 138 (2017) 57-67; V. Gandin, A. P. Fernandes, M. P. Rigobello, B. Dani, F. Sorrentino, F. Tisato, M. Bjornstedt, A. Bindoli, A. Sturaro, R. Rella and C. Marzano, Biochem. Pharmacol., 2010, 79, 90-101; D. de Vos, S. Y. Ho, E. R. T. Tiekink, Bioinorg. Chem. Appl. 2004, 2, 141-154; M. Altaf, M. Monim-ul-Mehboob, A. A. A. Seliman, M. Sohail, M. I. M. Wazeer, A. A. Isab, L. Li, V. Dhuna, G. Bhatia, K. Dhuna, Eur. J. Med. Chem. 95 (2015) 464-472; S. S. Al-Jaroudi, M. Altaf, A. A. Seliman, S. Yadav, F. Arjmand, A. Alhoshani, H. M. Korashy, S. Ahmad, A. A. Isab, Inorg. Chim. Acta, 464 (2017) 37-48; and A. A. A. Sulaiman, M. Altaf, A. A. Isab, A. Alawad, S. Ahmad, Z. Anorg. Allg. Chem., 642 (2016) 1454-1459, each incorporated herein by reference in their entirety]. The structural studies of these complexes have suggested that gold(I) atoms tend to form stable complexes with polarizable soft donor atoms, such as phosphorus and sulfur [F. K. Keter, I. A. Guzei, M. Nell, W. E. van Zyl, J. Darkwa, Inorg. Chem. 2014, 53, 2058-2067; M. Serratrice, M. A. Cinellu, L. Maiore, M. Pilo, A. Zucca, C. Gabbiani, A. Guerri, I. Landini, S. Nobili, E. Mini, L. Messori, Inorg. Chem. 2012, 51, 3161-3171; J. D. S. Chaves, F. Neumann, T. M. Francisco, C. C. Corrêa, M. T. P. Lopes, H. Silva, A. P. S. Fontes, and M. V. de Almeida, Inorg. Chim. Acta 414 (2014) 85-90; D. de Vos, S. Y. Ho, E. R. T. Tiekink, Bioinorg. Chem. Appl. 2004, 2, 141-154; M. Altaf, M. Monim-ul-Mehboob, A. A. A. Seliman, M. Sohail, M. I. M. Wazeer, A. A. Isab, L. Li, V. Dhuna, G. Bhatia, K. Dhuna, Eur. J. Med. Chem. 95 (2015) 464-472; S. S. Al-Jaroudi, M. Altaf, A. A. Seliman, S. Yadav, F. Arjmand, A. Alhoshani, H. M. Korashy, S. Ahmad, A. A. Isab, Inorg. Chim. Acta, 464 (2017) 37-48; and A. A. A. Sulaiman, M. Altaf, A. A. Isab, A. Alawad, S. Altuwaijri, S. Ahmad, Z. Anorg. Allg. Chem., 642 (2016) 1454-1459, each incorporated herein by reference in their entirety].

Because of their marked cytotoxicity and tumor specificity, phosphanogold(I) dithiocarbamate (i.e., phosphinogold (I) dithiocarbamate) complexes have been studied as a novel class of potential anticancer agents [F. K. Keter, I. A. Guzei, M. Nell, W. E. van Zyl, J. Darkwa, Inorg. Chem. 2014, 53, 2058-2067; V. Gandin, A. P. Fernandes, M. P. Rigobello, B. Dani, F. Sorrentino, F. Tisato, M. Bjornstedt, A. Bindoli, A. Sturaro, R. Rella and C. Marzano, Biochem. Pharmacol., 2010, 79, 90-101; D. de Vos, S. Y. Ho, E. R. T. Tiekink, Bioinorg. Chem. Appl. 2004, 2, 141-154; M. Altaf, M. Monim-ul-Mehboob, A. A. A. Seliman, M. Sohail, M. I. M. Wazeer, A. A. Isab, L. Li, V. Dhuna, G. Bhatia, K. Dhuna, Eur. J. Med. Chem. 95 (2015) 464-472; and S. S. Al-Jaroudi, M. Altaf, A. A. Seliman, S. Yadav, F. Arjmand, A. Alhoshani, H. M. Korashy, S. Ahmad, A. A. Isab, Inorg. Chim. Acta, 464 (2017) 37-48, each incorporated herein by reference in their entirety]. Keter et al. [F. K. Keter, I. A. Guzei, M. Nell, W. E. van Zyl, J. Darkwa, Inorg. Chem. 2014, 53, 2058-2067, incorporated herein by reference in its entirety] studied the anticancer properties of a series of phosphanogold(I) complexes of dithiocarbamate including [AuL(PPh$_3$)] and [Au$_2$L$_2$(diphosphanes)] (L=dithiocarbamate). The stability of these complexes was found to depend on the nature of the phosphane ligand. Specifically, triphenylphosphane and diphenylphosphanoalkyl ligands with alkyl chains longer than ethyl yielded stable gold dithiocarbamates in solution, while diphenylphosphanoethanegold(I) complexes were found to be unstable and transformed to an Au$_{18}$ cluster. Keter et al. further noted that all the complexes stable in solution displayed cytotoxic activity against HeLa cancer cells, suggesting the importance of the P—Au—S moiety in conferring activity to the compounds [C. K. Mirabelli, R. K. Johnson, C. M. Sung, L. Faucette, K. Muirhead, S. T. Crooke, Cancer Res. 1985, 45, 32-39; Tiekink, E. R. T. Bioinorg. Chem. Appl. 2003, 1, 53; and F. K. Keter, I. A. Guzei, M. Nell, W. E. van Zyl, J. Darkwa, Inorg. Chem. 2014, 53, 2058-2067, each incorporated herein by reference in their entirety].

It has been established that gold compounds, such as auranofin, act against cancer cells via the mitochondria pathway by inhibiting the activity of thioredoxin reductase (TrxR) enzyme [C. Marzano, V. Gandin, A. Folda, G. Scutari, A. Bindoli, M. P. Rigobello, Free Radical Biology & Medicine 42 (2007) 872-881; V. Gandin, A. P. Fernandes, M. P. Rigobello, B. Dani, F. Sorrentino, F. Tisato, M. Bjornstedt, A. Bindoli, A. Sturaro, R. Rella and C. Marzano, Biochem. Pharmacol., 2010, 79, 90-101; M. J. McKeage, L. Maharaj and S. J. Berners-Price, Coord. Chem. Rev., 232 (2002) 127-135; and W. Fiskus, N. Saba, M. Shen, M. Ghias, J. Liu, S. D. Gupta, L. Chauhan, R. Rao, S. Gunewardena, K. Schorno, C. P. Austin, K. Maddocks, J. Byrd, A. Melnick, P. Huang, A. Wiestner, K. N. Bhalla, Cancer Res. 74 (2014) 2520-2532, each incorporated herein by reference in their entirety]. The inhibition of TrxR demonstrated by the gold compounds has been evidenced by the covalent binding between the gold(I) center and selenocysteine residue in the target site of the enzyme [I. Ott, Coord. Chem. Rev. 253 (2009) 1670-1681; S. J. Berners-Price, A. Filipovska, Metallomics 3 (2011) 863-873; and M. J. McKeage, L. Maharaj and S. J. Berners-Price, Coord. Chem. Rev., 232 (2002) 127-135, each incorporated herein by reference in their entirety]. Several studies suggested that the lipophilicity of gold(I) complexes could be tailored for them to act against cancers cells via the mitochondria pathway [S. J. Berners-Price, A. Filipovska, Metallomics 3 (2011) 863-873; V. Gandin, A. P. Fernandes, M. P. Rigobello, B. Dani, F. Sorrentino, F. Tisato, M. Bjornstedt, A. Bindoli, A. Sturaro, R. Rella and C. Marzano, Biochem. Pharmacol., 2010, 79, 90-101; and M. J. McKeage, L. Maharaj and S. J. Berners-Price, Coord. Chem. Rev., 232 (2002) 127-135, each incorporated herein by reference in their entirety].

Recently, structural elucidation and anticancer activity of gold(I) dithiocarbamate complexes have been reported [M. Altaf, M. Monim-ul-Mehboob, A. A. A. Seliman, M. Sohail, M. I. M. Wazeer, A. A. Isab, L. Li, V. Dhuna, G. Bhatia, K. Dhuna, Eur. J. Med. Chem. 95 (2015) 464-472; S. S. Al-Jaroudi, M. Altaf, A. A. Seliman, S. Yadav, F. Arjmand, A. Alhoshani, H. M. Korashy, S. Ahmad, A. A. Isab, Inorg. Chim. Acta, 464 (2017) 37-48; A. A. Sulaiman, M. Altaf, A. A. Isab, A. Alawad, S. Altuwaijri, S. Ahmad, Z. Anorg. Allg. Chem., 642 (2016) 1454-1459; and M. Altaf, M. Monim-ul-mehboob, A. A. Seliman, A. A. Isab, V. Dhuna, G. Bhatia, K. Dhuna, J. Organomet. Chem. 765 (2014) 68-79, each incorporated herein by reference in their entirety]. Gold(I) atoms in these complexes have been observed to possess a linear geometry. Many reported complexes have demonstrated greater in vitro cytotoxicity against cancer cells (e.g., A549, HeLa, HepG2) than cisplatin. Despite these recent advances there is still a need to develop new gold(I) complexes with improved anticancer efficacy and specificity.

In view of the forgoing, one objective of the present disclosure is to provide mixed ligand phosphinogold(I) complexes containing a dithiocarbamate or halogen ligand, pharmaceutical compositions containing the gold(I) complexes, and a method of treating cancer with the gold(I) complexes.

BRIEF SUMMARY OF THE INVENTION

According to a first aspect, the present disclosure relates to a gold(I) complex of formula (I)

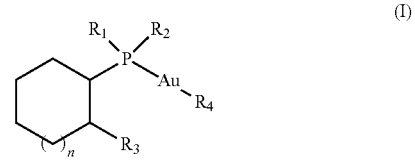

or a salt thereof, a solvate thereof, a tautomer thereof, a stereoisomer thereof, or a mixture thereof, wherein (i) $R_1$ and $R_2$ are each independently an optionally substituted aryl, (ii) $R_3$ is selected from the group consisting of —OH, —OCH$_3$, —NH$_2$, and —N(CH$_3$)$_2$, (iii) $R_4$ is a halogen or

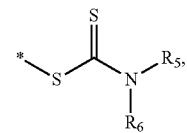

wherein $R_5$ and $R_6$ are each independently selected from the group consisting of a hydrogen, an optionally substituted alkyl, an optionally substituted cycloalkyl, an optionally substituted arylalkyl, and an optionally substituted aryl, and (iv) n is an integer in a range of 1-3.

In one embodiment, $R_1$ and $R_2$ are each independently an optionally substituted phenyl.

In one embodiment, $R_1$ and $R_2$ are each phenyl.

In one embodiment, $R_3$ is —NH$_2$.

In one embodiment, n is 1.

In one embodiment, $R_4$ is chloro.

In one embodiment, $R_4$ is

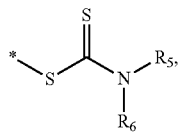

and $R_5$ and $R_6$ are each independently a $C_1$ to $C_8$ alkyl or a $C_7$ to $C_{12}$ arylalkyl.

In a further embodiment, $R_5$ and $R_6$ are each methyl, ethyl, or benzyl.

In one embodiment, the gold(I) complex of formula (I) is selected from the group consisting of

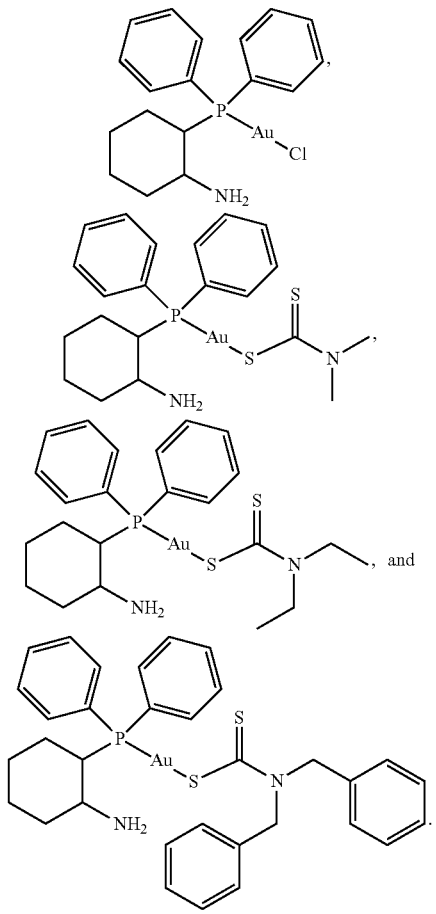

In one embodiment, the gold(I) complex of formula (I) is selected from the group consisting of

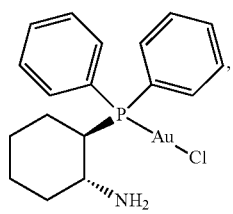

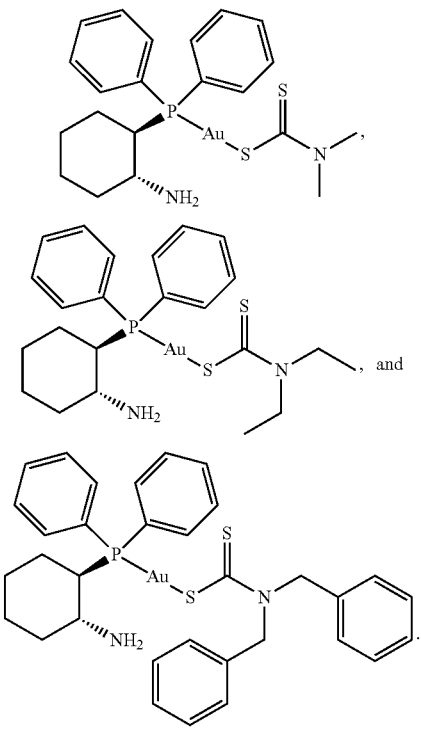

According to a second aspect, the present disclosure relates to a pharmaceutical composition containing the gold (I) complex of formula (I) of the first aspect and a pharmaceutically acceptable carrier and/or excipient.

In one embodiment, the pharmaceutical composition contains 0.5-50 μM of the gold(I) complex of formula (I) relative to a total volume of the pharmaceutical composition.

In one embodiment, the pharmaceutically acceptable carrier and/or excipient is at least one selected from the group consisting of a buffer, an inorganic salt, a fatty acid, a vegetable oil, a synthetic fatty ester, a surfactant, and a polymer.

In one embodiment, the gold(I) complex of formula (I) is selected from the group consisting of

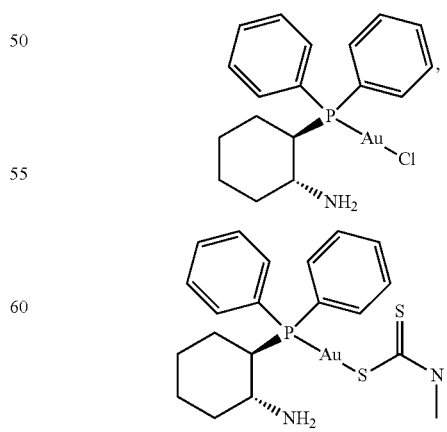

-continued

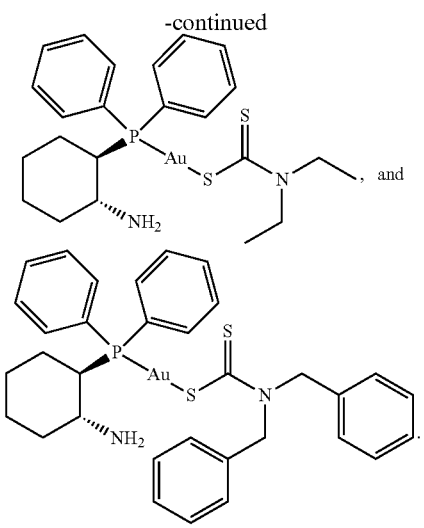

According to a third aspect, the present disclosure relates to a method for treating a proliferative disorder. The method involves administering the pharmaceutical composition of the second aspect to a subject in need of therapy.

In one embodiment, 0.01-50 mg/kg of the gold(I) complex of formula (I) is administered per body weight of the subject.

In one embodiment, the proliferative disorder is cancer.

In one embodiment, the cancer is at least one selected from the group consisting of lung cancer, cervical cancer, and liver cancer.

In one embodiment, the cancer is resistant to at least one platinum-based chemotherapy drug.

In one embodiment, the platinum-based chemotherapy drug is cisplatin.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
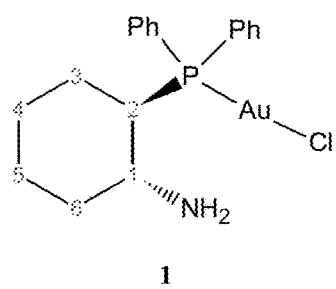
FIG. 1 illustrates chemical structures of gold(I) complexes 1, 2, 3, and 4.
Figure 1:
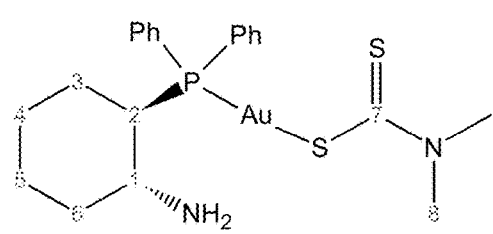
Figure 1:
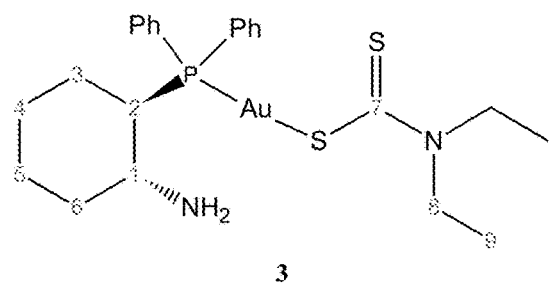
Figure 1:
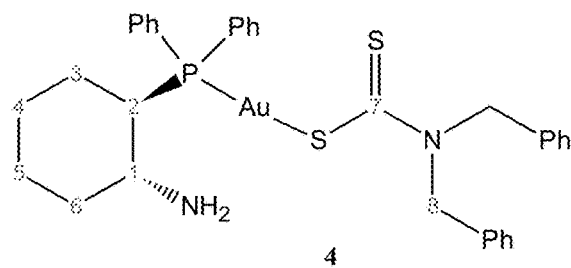

Embodiments of the present disclosure will now be described more fully hereinafter with reference to the accompanying drawings, in which some, but not all embodiments of the disclosure are shown.

As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

As used herein, the terms "complex", "compound", and "product" are used interchangeably, and are intended to refer to a chemical entity, whether in the solid, liquid or gaseous phase, and whether in a crude mixture or purified and isolated.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, iso-propanol, n-butanol, iso-butanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those of ordinary skill in the art.

As used herein, the term "tautomer" refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), and open-chain and cyclic forms of an acetal or hemiacetal (e.g., in reducing sugars).

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images.

Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans-(E- and Z-) isomers, and non-enantiomeric optical isomers. Diastereomers seldom have the same physical properties. In terms of the present disclosure, stereoisomers may refer to enantiomers, diastereomers, or both.

Conformers, rotamers, or conformational isomers refer to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. It should be understood that all conformers, rotamers, or conformational isomer forms, insofar as they may exist, are included within the present disclosure.

In terms of the present disclosure, stereoisomers of the ring systems, stereogenic centers, and the like can all be present in the compounds, and all such stable isomers are contemplated in the present disclosure. S- and R-(or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

The term "aryl", as used herein, and unless otherwise specified, refers to a substituent that is derived from an aromatic hydrocarbon (arene) that has had a hydrogen atom removed from a ring carbon atom. The aryl group may be a carbocyclic aromatic monocyclic group containing 6 carbon atoms which may be further fused to one or more 5- or 6-membered carbocyclic group which may be aromatic, saturated or unsaturated. Aryl includes, but is not limited to, phenyl, biphenyl, 1-naphthyl, 2-naphthyl, anthracenyl, and the like.

As used herein, the term "alkyl" unless otherwise specified refers to both branched and straight chain saturated aliphatic primary, secondary, and/or tertiary hydrocarbons of typically $C_1$ to $C_{21}$, for example $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, 2-propylheptyl, tetradecyl, pentadecyl, hexadecyl, heptadecyl, octadecyl, nonadecyl, and eicosyl.

The term "cycloalkyl" refers to cyclized alkyl groups. Exemplary cycloalkyl groups include, but are not limited to, cyclopropyl, cyclobutyl, cyclopentyl, cyclohexyl, cycloheptyl, cyclooctyl, norbornyl, and adamantyl. Branched cycloalkyl groups such as exemplary 1-methylcyclopropyl and 2-methylcyclopropyl groups and cycloalkenyl groups such as cyclobutenyl, cyclopentenyl, and cyclohexenyl are included in the definition of cycloalkyl as used in the present disclosure.

The term "arylalkyl", as used herein, refers to a straight or branched chain alkyl moiety (as defined above) that is substituted by an aryl group (as defined above), and includes, but is not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

The term "halogen", as used herein, means fluoro, chloro, bromo and iodo.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —$SO_2NH_2$), substituted sulfonamide, nitro, cyano, carboxy, unsubstituted amide (i.e. —$CONH_2$), substituted amide (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof. The substituents may themselves be optionally substituted, and may be either unprotected, or protected as necessary, as known to those of ordinary skill in the art, for example, as taught in Greene, et al., "Protective Groups in Organic Synthesis", John Wiley and Sons, Second Edition, 1991, hereby incorporated by reference in its entirety.

The present disclosure is intended to include all isotopes of atoms occurring in the present compounds. Isotopes include those atoms having the same atomic number but different mass numbers. By way of general example, and without limitation, isotopes of hydrogen include deuterium and tritium, and isotopes of carbon include $^{13}C$ and $^{14}C$. Isotopically labeled compounds of the disclosure can generally be prepared by conventional techniques known to those skilled in the art or by processes and methods analogous to those described herein, using an appropriate isotopically labeled reagent in place of the non-labeled reagent otherwise employed.

The present disclosure provides gold(I) complexes having medicinal or pharmaceutical properties, preferably antitumor or anticancer properties. In these gold(I) complexes, the gold(I) atom is coordinated in a mixed ligand environment. Preferably, the gold(I) atom is coordinated by (i) a phosphine ligand and (ii) either a halogen or a dithiocarbamate ligand. The coordination of each of the phosphine, halogen, and dithiocarbamate ligand to a gold(I) atom is preferably in a monodentate fashion. In preferred embodiments, the gold (I) complex is mononuclear (i.e., contains one gold(I) atom), with a single phosphine ligand and a single halogen or dithiocarbamate ligand coordinated to the gold(I) atom in a monodentate fashion via gold-phosphine bonding and gold-halogen or gold-sulfur interaction, respectively.

The present disclosure provides a gold(I) complex of formula (I)

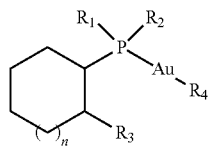

(I)

or a salt thereof, a solvate thereof, a tautomer thereof, a stereoisomer thereof, or a mixture thereof.

$R_1$ and $R_2$ of the phosphine ligand of the gold(I) complex of formula (I) may be the same or different. Preferably $R_1$ and $R_2$ are the same. $R_1$ and $R_2$ are each independently an optionally substituted aryl. Preferably, $R_1$ and $R_2$ are each independently a $C_6$ to $C_{16}$ aryl, preferably a $C_7$ to $C_{14}$ aryl, preferably a $C_8$ to $C_{12}$ aryl, preferably a $C_9$ to $C_{10}$ aryl. For example, $R_1$ and $R_2$ may be each independently an optionally substituted phenyl, an optionally substituted biphenyl, an optionally substituted naphthyl, and an optionally substituted anthracenyl. In preferred embodiments, $R_1$ and $R_2$ are each independently an optionally substituted phenyl. Most preferably, $R_1$ and $R_2$ are the same, and are each phenyl.

As used herein, the value of n denotes an alkyl chain of —$CH_2$— groups within the cycloalkyl ring of the phosphine ligand of the gold(I) complex of formula (I). In one or more embodiments, n is an integer in a range of 1-6, preferably 2-5, preferably 3-4. Most preferably, n is 1. In some embodiments, the cycloalkyl ring is a $C_{6-11}$ cycloalkyl, a $C_{7-10}$ cycloalkyl, or a $C_{8-9}$ cycloalkyl. Most preferably, the cycloalkyl ring is a $C_6$ cycloalkyl (i.e., cyclohexyl). The carbon counts described herein refer to a number of cycloalkyl ring carbon atoms of the phosphine ligand which excludes the carbon atoms of optionally present substituents of the cycloalkyl ring.

$R_3$ of the cycloalkyl ring of the phosphine ligand of the gold(I) complex of formula (I) may be an electron-donating group. Non-limiting examples of electron-donating groups include alkyls (e.g., methyl, ethyl), aryls (e.g., phenyl), amines (e.g., primary, secondary, and tertiary amines), amides, and oxygen containing groups (e.g., hydroxy, alkoxy). In preferred embodiments, $R_3$ is selected from the group consisting of —OH, —$OCH_3$, —$NH_2$, and —$N(CH_3)_2$. Most preferably, $R_3$ is —$NH_2$.

The $R_3$ and —$P(R_1)(R_2)$ groups of cycloalkyl ring of the phosphine as a free ligand may be arranged in cis (e.g.,

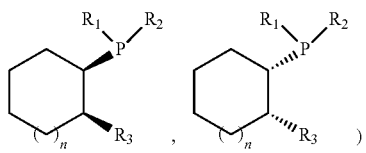

) or trans configuration (e.g.,

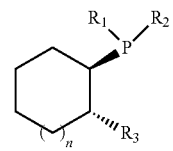

(R, R),

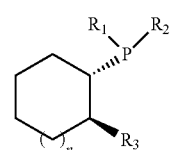

(S, S)). Preferably, the $R_3$ and $P(R_1)(R_2)$ groups of cycloalkyl ring of the phosphine ligands of the gold(I) complex of formula (I) are arranged in trans configuration. The (R, R) enantiomer (i.e.

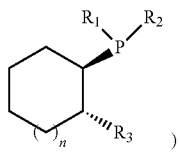

) of the trans diastereomers of the gold(I) complex of formula (I) is most preferably.

In some embodiments, the $R_4$ ligand of the gold(I) complex of formula (I) is a dithiocarbamate having the following formula:

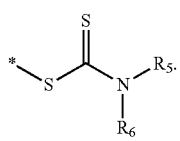

$R_5$ and $R_6$ of the dithiocarbamate ligand, when present in the gold(I) complex, may be the same or different. Preferably $R_5$ and $R_6$ are the same. $R_5$ and $R_6$ are each independently selected from the group consisting of a hydrogen, an optionally substituted alkyl, an optionally substituted cycloalkyl, an optionally substituted arylalkyl, and an optionally substituted aryl. In some embodiments, $R_5$ and $R_6$ are each independently an optionally substituted alkyl or an optionally substituted arylalkyl. Preferably, $R_5$ and $R_6$ are each independently a $C_1$ to $C_8$ alkyl, preferably a $C_2$ to $C_7$ alkyl, preferably a $C_3$ to $C_6$ alkyl, preferably a $C_4$ to $C_5$ alkyl, or a $C_7$ to $C_{12}$ arylalkyl, preferably a $C_8$ to $C_{11}$ arylalkyl, preferably a $C_9$ to $C_{10}$ arylalkyl. In preferred embodiments, $R_5$ and $R_6$ are the same, and are each methyl, ethyl, or benzyl. Most preferably, $R_5$ and $R_6$ are each methyl.

In a further embodiment, the gold(I) complex of formula (I) is selected from the group consisting of:

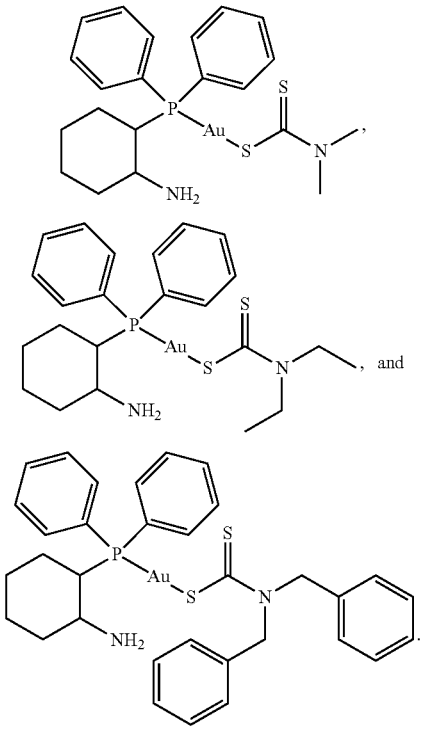

Preferably, the phosphino and the amino groups are arranged in trans configuration, and the gold(I) complex of formula (I) is selected from the group consisting of:

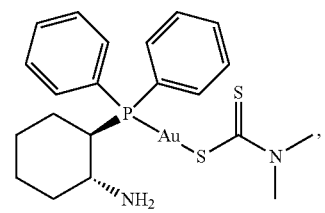

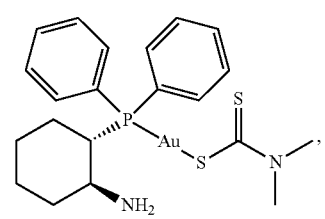

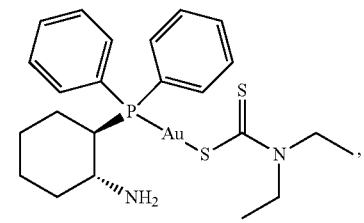

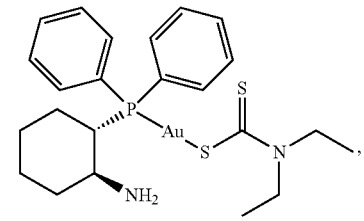

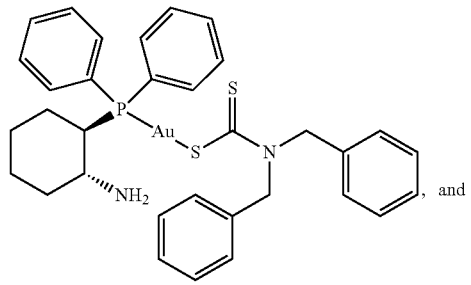

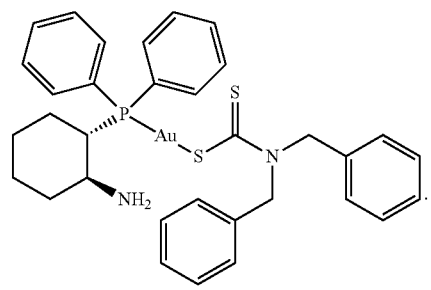

Most preferably, the gold(I) complex of formula (I) is selected from the group consisting of

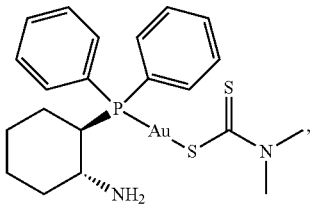

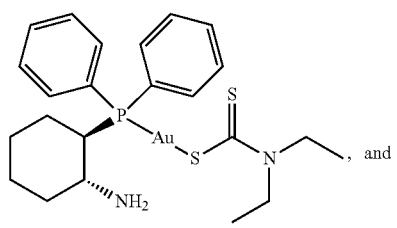

-continued

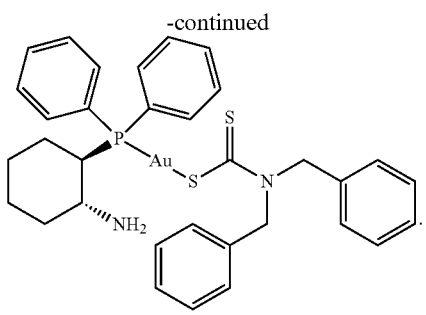

Alternatively, the $R_4$ ligand of the gold(I) complex of formula (I) is a halogen, such as fluoro, chloro, bromo and iodo. Preferably $R_4$ is chloro or bromo. Most preferably $R_4$ is chloro.

In a further embodiment, the gold(I) complex of formula (I) is

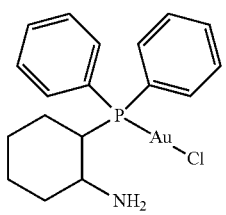

Preferably, the phosphino and the amino groups are arranged in trans configuration, and the gold(I) complex of formula (I) is

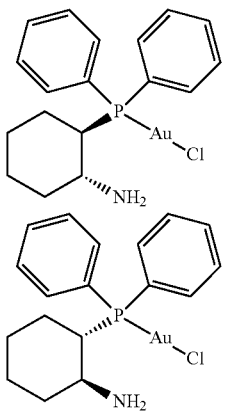

or a mixture thereof.

Most preferably, the gold(I) complex of formula (I) is

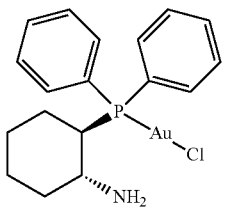

The gold(I) complexes of the present disclosure may be prepared by any complexation method know to those of ordinary skill in the art. The following methods set forth below are provided for illustrative purposes and not intended to limit the scope of the disclosure.

For example, when the $R_4$ ligand of the gold(I) complex of formula (I) is a halogen, the gold(I) complex may be synthesized by mixing a gold(I) precursor of formula (II)

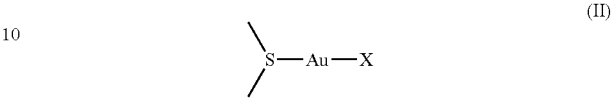

(II)

or a salt thereof, a solvate thereof, or a mixture thereof, a phosphine compound of formula (III)

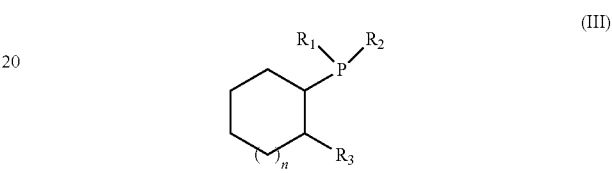

(III)

or a salt thereof, a solvate thereof, a stereoisomer thereof, or a mixture thereof, and a solvent, thereby forming the gold(I) complex of formula (I), wherein X is a halogen, and $R_1$, $R_2$, $R_3$, and n are specified above.

Figure 2:
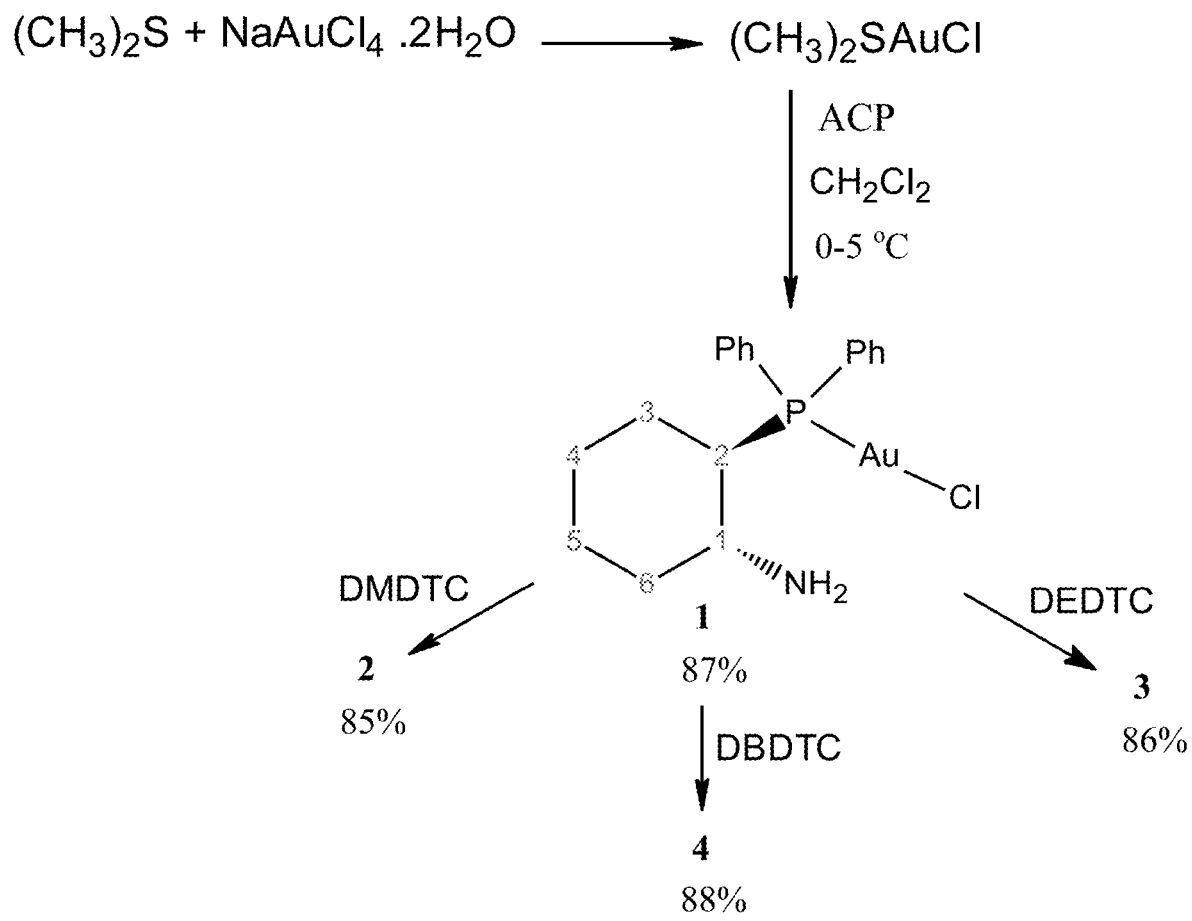
FIG. 2 is a scheme illustrating the synthesis of gold(I) complexes 1, 2, 3, and 4.

Exemplary gold(I) precursors of formula (II) include, but are not limited to, chloro(dimethyl sulfide)gold(I) and bromo(dimethyl sulfide)gold(I). Other gold(I) precursors including, but not limited to, chloro(tetrahydrothiophene) gold(I), and bromo(tetrahydrothiophene)gold(I) may be used in addition to or in lieu of the gold(I) precursors of formula (II). The gold(I) precursors may be available from commercial vendors such as Sigma Aldrich, and TCI America. Alternatively, as shown in FIG. 2, the gold(I) precursors can be prepared by previously reported synthesis and methods with slight modifications as recognized as appropriate by a person of ordinary skill in the pharmaceutical or medicinal chemistry art [S. Ahmad, M. N. Akhtar, A. A. Isab, A. R. Al-Arfaj, M. S. Hussain, J. Coord. Chem. 51 (2000) 225-234, incorporated herein by reference in its entirety].

In a preferred embodiment, mixing the gold(I) precursor of formula (II) and the phosphine compound of formula (III) is performed in an organic solvent to form a first reaction mixture. Exemplary organic solvents include, but are not limited to, aromatic solvents (e.g., benzene, ethylbenzene, o-xylene, m-xylene, p-xylene, and mixtures of xylenes, toluene, mesitylene, anisole, 1,2-dimethoxybenzene, α,α, α,-trifluoromethylbenzene, fluorobenzene, heavy aromatic naptha), alkane solvents (e.g., pentane, cyclopentane, hexanes, cyclohexane, heptanes, cycloheptane, octanes), ethers (e.g. diethyl ether, tetrahydrofuran, 1,4-dioxane, tetrahydropyran, t-butyl methyl ether, cyclopentyl methyl ether, di-isopropyl ether), glycol ethers (e.g. 1,2-dimethoxyethane, diglyme, triglyme), chlorinated solvents (e.g. chlorobenzene, dichloromethane, 1,2-dichloroethane, 1,1-dichloroethane, chloroform, carbon tetrachloride), ester solvents (e.g. ethyl acetate, propyl acetate), ketones (e.g. acetone, butanone), formamides/acetamides (e.g., formamide, dimethyl formamide, dimethyl acetamide), monoalcohols (e.g., methanol, ethanol, propanol, isopropanol, n-butanol, isobutanol, n-pentanol, n-hexanol, terpineol, menthol, prenol, 3-methyl-3-buten-1-ol, 2-ethyl-1-hexanol, 2-ethyl-1-butanol, 2-propylheptan-1-ol, 2-butyl-1-octanol, benzyl alcohol), polyalcohols including glycols (e.g., ethylene glycol, diethylene glycol, triethylene glycol, tetraethylene glycol, propylene glycol, dipropylene glycol, 1,3-propanediol, 1,3-butanediol, 1,4-butanediol, 1,6-hexanediol, glycerol, pentaerythritol, manitol, sorbitol), as well as mixtures thereof. Preferably a chlorinated solvent (e.g., dichloromethane) is used as the solvent.

Typically, the gold(I) precursor of formula (II) is present in the first reaction mixture at a concentration in a range of 1-600 mM, preferably 5-500 mM, preferably 10-400 mM, preferably 20-200 mM, preferably 30-100 mM, or about 35 mM. In a related embodiment, the phosphine compound of formula (III) is present in the first reaction mixture at a concentration in a range of 1-600 mM, preferably 5-500 mM, preferably 10-400 mM, preferably 20-200 mM, preferably 30-100 mM, or about 35 mM. In one or more embodiments, a molar ratio of the gold(I) precursor to the phosphine compound is in the range of 1:2 to 2:1, preferably 2:3 to 3:2, preferably 1:1.2 to 1.2:1, or about 1:1.

The first reaction mixture may be agitated (e.g., using an agitator, a vortexer, a rotary shaker, a magnetic stirrer, a centrifugal mixer, an overhead stirrer) at a temperature of −10-10° C., −4-8° C., or 0-5° C. for any amount of time sufficient for complexation, typically from 0.1 to 8 hours, preferably from 0.25 to 4 hours, preferably 0.5-2 hours, or about 1 hour.

The first reaction mixture may then be concentrated by evaporating the solvent to yield a crude gold(I) complex of formula (I), where $R_4$ is a halogen. The crude gold(I) complex may be further purified by methods known to those skilled in the art, for example, aqueous workup, extraction with solvents, distillation, recrystallization, column chromatography, and high-performance liquid chromatography (HPLC). Precipitation/crystallization of the gold(I) complex may occur, and the precipitate/crystals may be collected using methods known to those of ordinary skill in the art such as filtration.

Alternatively, when $R_4$ ligand of the gold(I) complex of formula (I) is a dithiocarbamate having the following formula:

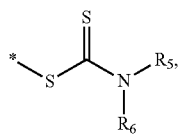

the gold(I) complex may be synthesized by mixing the gold(I) precursor of formula (II) (as described above)

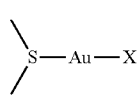

(II)

or a salt thereof, a solvate thereof, or a mixture thereof, the phosphine compound of formula (III) (as described above)

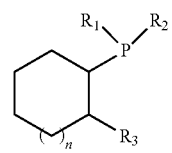

(III)

or a salt thereof, a solvate thereof, a stereoisomer thereof, or a mixture thereof, a dithiocarbamate salt of formula (IV)

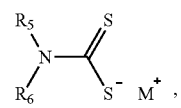

(IV)

and a solvent, thereby forming the gold(I) complex of formula (I), wherein $R_1$, $R_2$, $R_3$, $R_5$, $R_6$, X, and n are specified above.

M is an alkali metal cation (e.g. sodium, potassium, cesium, lithium, silver, and rubidium), an ammonium cation, an optionally substituted alkylammonium cation (e.g. dimethylammonium, diethylammonium, triethylammonium, tetrabutylammonium, tributylmethylammonium, trioctylmethylammonium, and benzylammonium cations), an optionally substituted arylammonium cation (e.g. phenylammonium, and diphenylammonium cations), or an optionally substituted alkylarylammonium cation (e.g. dimethylphenylammonium, and trimethylphenylammonium cations). Most preferably, M is sodium cation.

Exemplary dithiocarbamate salts include, but are not limited to, sodium dimethyldithiocarbamate, potassium dimethyldithiocarbamate, sodium diethyldithiocarbamate, potassium diethyldithiocarbamate, and sodium dibenzyldithiocarbamate.

In a preferred embodiment, mixing the gold(I) precursor of formula (II), the phosphine compound of formula (III) and the dithiocarbamate salt of formula (IV) is performed in one or more organic solvents to form a second reaction mixture. Preferably a mixture of a chlorinated solvent (e.g., dichloromethane) and a monoalcohol (e.g., ethanol) is used as the solvent, for example at a vol:vol ratio of 2:3 to 4:1, preferably 1:1 to 3:1, or about 3:2.

Typically, the gold(I) precursor of formula (II) is present in the second reaction mixture at a concentration in a range of 1-500 mM, preferably 5-250 mM, preferably 10-100 mM, preferably 15-50 mM, preferably 18-25 mM, or about 20 mM. In a related embodiment, the phosphine compound of formula (III) is present in the second reaction mixture at a concentration in a range of 1-500 mM, preferably 5-250 mM, preferably 10-100 mM, preferably 15-50 mM, preferably 18-25 mM, or about 20 mM. In another related embodiment, the dithiocarbamate salt of formula (IV) is present in the second reaction mixture at a concentration in a range of 1-500 mM, preferably 5-250 mM, preferably 10-100 mM, preferably 15-50 mM, preferably 18-25 mM, or about 20 mM. In one or more embodiments, a molar ratio of the gold(I) precursor to the phosphine compound is in the range of 1:2 to 2:1, preferably 2:3 to 3:2, preferably 1:1.2 to 1.2:1, or about 1:1, and a molar ratio of the gold(I) precursor to the dithiocarbamate salt is in the range of 1:2 to 2:1, preferably 2:3 to 3:2, preferably 1:1.2 to 1.2:1, or about 1:1.

The second reaction mixture may be agitated at a temperature of 4-50° C., 10-40° C., 15-35° C., or 20-25° C. for any amount of time sufficient for complexation, typically from 0.5 to 12 hours, preferably from 1 to 6 hours, preferably 1.5-3 hours, or about 2 hours.

The second reaction mixture may then be filtered to collect a solution. The solution may be concentrated by evaporating the solvent to yield a crude gold(I) complex of formula (I) where $R_4$ is the dithiocarbamate

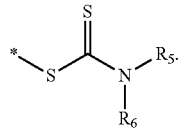

The crude gold(I) complex of formula (I) may be further purified by methods known to those skilled in the art, for example, aqueous workup, extraction with solvents, distillation, recrystallization, column chromatography, and high-performance liquid chromatography (HPLC). Precipitation/crystallization of the gold(I) complex may occur, and the precipitate/crystals may be collected using methods known to those of ordinary skill in the art such as filtration.

According to a further aspect, the present disclosure relates to a pharmaceutical composition containing the gold (I) complex of formula (I) of the first aspect and a pharmaceutically acceptable carrier and/or excipient.

As used herein, a "composition" or a "pharmaceutical composition" refers to a mixture of the active ingredient with other chemical components, such as pharmaceutically acceptable carriers and excipients. One purpose of a composition is to facilitate administration of the compound disclosed herein in any of its embodiments to a subject. Pharmaceutical compositions of the present disclosure may be manufactured by processes well known in the art, e.g., by means of conventional mixing, dissolving, granulating, dragee-making, levigating, emulsifying, encapsulating, entrapping or lyophilizing processes. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient", as used herein, refers to an ingredient in the composition that is biologically active, for example, one or more of the gold(I) complexes represented by formula (I), salts thereof, solvates thereof, tautomers thereof, stereoisomers thereof, or any mixtures thereof. In some embodiments, other active ingredients in addition to the complexes of the current disclosure may be incorporated into a pharmaceutical composition, for example, a second active ingredient which is chemically distinct from the gold(I) complexes.

In one or more embodiments, the gold(I) complex of formula (I) of the pharmaceutical composition is selected from the group consisting of

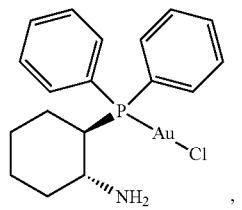

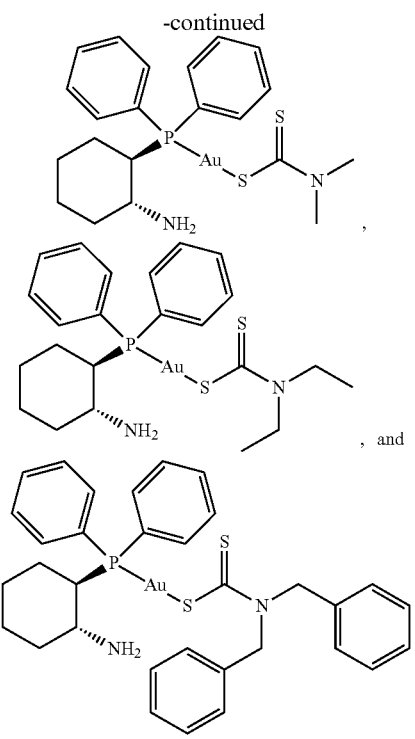

Most preferably, the gold(I) complex of formula (I) of the pharmaceutical composition is

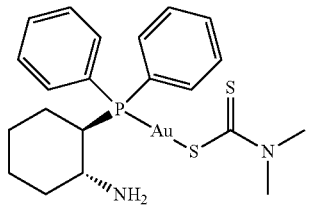

When the gold(I) complexes are administered as pharmaceuticals, to humans and animals, they can be given per se or as a pharmaceutical composition containing the active ingredient(s) in combination with a pharmaceutically acceptable carrier and/or excipient. The pharmaceutical composition may contain at least 0.0001 wt. %, at least 0.001 wt. %, at least 0.01 wt. %, at least 0.05 wt. %, at least 0.1 wt. %, at least 0.5 wt. %, at least 5 wt. %, at least 10 wt. %, at least 15 wt. %, at least 20 wt. %, at least 25 wt. %, at least 30 wt. %, at least 35 wt. %, at least 40 wt. %, at least 45 wt. %, at least 50 wt. %, at least 55 wt. %, at least 60 wt. %, at least 65 wt. %, at least 70 wt. %, at least 75 wt. %, at least 80 wt. %, at least 85 wt. %, at least 90 wt. %, at least 95 wt. %, at least 99 wt. %, or at least 99.9 wt. % of the gold(I) complex of formula (I) relative to a total weight of the pharmaceutical composition. For example, when formulated as a solution, the pharmaceutical composition may contain 0.1-100 μM of the gold(I) complex of formula (I) relative to a total volume of the pharmaceutical composition, preferably 0.5-50 μM, preferably 1-45 μM, preferably 2-40 μM, preferably 3-35 μM, preferably 4-30 μM, preferably 5-25 μM, preferably 6-20 μM, preferably 7-15 μM, preferably 8-12 μM, preferably 10-11 μM of the gold(I) complex relative to a total volume of the pharmaceutical composition.

In some embodiments, the active ingredient of the current disclosure, e.g. the gold(I) complex of formula (I), a salt thereof, a solvate thereof, a tautomer thereof, a stereoisomer thereof, or any mixtures thereof, provides utility as an anticancer agent in reducing the viability of cancer cells derived from human cancer cell lines including, but not limited to, lung cancer cell lines (e.g., A549, NCI-H460, SHP-77, COR-L23/R, NCI-H69/LX20); cervical cancer cell lines (e.g., HeLa, ME-180, R-ME-180); liver cancer cell lines (e.g., HepG2, PLC/PRF/5, THLE-3, C3A, SNU-182, SNU-398, SNU-387, SNU-423, SNU-475, SNU-449, and Hep 3B2.1-7); ovarian cancer cell lines (e.g., NCI-ADR/RES, OVCAR-03, A2780, A2780cis, OV7, PE023); breast cancer cell lines (e.g., MDA-MB-231, MCF-7, SK-BR-3, T47D, VP303); stomach cancer cell lines (e.g., N87, SNU-16, SNU-5, SNU-1, KATO III, AGS); colon/colorectal cancer cell lines (e.g., HCT-116, CACO-2, HT-29, HCT15, MDST8, GP5d, DLD1, SW620, SW403, T84); prostate cancer cell lines (e.g., DU145, PC-3); leukemia cell lines (e.g., HL-60, CESS, CCRF-CEM, CEM/C1, KASUMI-1, ARH-77); brain tumor cell lines (e.g., U251); renal cancer cell lines (e.g., 786-0); skin cancer or melanoma cell lines (e.g., UACC-62, C32TG, A375, MCC26); and bone cancers such as osteosarcoma cell lines (e.g., MG-63). Preferably, the active ingredient of the current disclosure, e.g. the gold(I) complex of formula (I), a salt thereof, a solvate thereof, a tautomer thereof, a stereoisomer thereof, or any mixtures thereof, provides utility as an anticancer agent in reducing the viability of cancer cells derived from lung cancer cell lines (e.g., A549, NCI-H460, SHP-77, COR-L23/R, NCI-H69/LX20), cervical cancer cell lines (e.g., HeLa, ME-180, R-ME-180), and liver cancer cell lines (e.g., HepG2, PLC/PRF/5, THLE-3, C3A, SNU-182, SNU-398, SNU-387, SNU-423, SNU-475, SNU-449, and Hep 3B2.1-7).

In some embodiments, the cancer cells are collected from a human patient who is at risk of having, is suspected of having, has been diagnosed with, or is being monitored for recurrence of at least one type of cancer, preferably lung cancer, cervical cancer, and/or liver cancer.

In preferred embodiments, the active ingredient of the present disclosure, e.g., the gold(I) complexes of formula (I), a salt thereof, a solvate thereof, a tautomer thereof, a stereoisomer thereof, or any mixtures thereof, may provide utility as an anticancer agent in reducing viability of cancer cells derived from human cancer cell lines which are resistant to, or which are susceptible to becoming resistant to, other therapeutic agents/chemotherapy agents such as platinum-based chemotherapy drugs including, but not limited to, cisplatin, carboplatin, and oxaliplatin. In at least one embodiment, the cancer cells are cisplatin-resistant cancer cells. These cells may be generated by culturing cancer cells with low doses of cisplatin in order to build their resistance to cisplatin while maintaining cell viability. Examples of cisplatin-resistant cancer cells include, but are not limited to, cisplatin resistant cervical cancers (e.g., R-ME-180), A549 cisplatin-resistant lung cancer cells, MCF-7 cisplatin-resistant breast cancer cells, A2780cis cisplatin-resistant ovarian cancer cells, and SGC7901cis cisplatin-resistant gastrointestinal cancer cells.

In some embodiments, the ability of the active ingredient to reduce the viability of cancer cells may be determined by contacting the pharmaceutical composition with the cancer cells and then performing cell viability assays. Methods of such assays include, but are not limited to, sulforhodamine-B (SRB) assay, ATP test, Calcein AM assay, clonogenic assay, ethidium homodimer assay, Evans blue assay, 2',7'-dichlorofluorescin diacetate (DCFDA) or 2',7'-dichlorodihydrofluorescein diacetate (H2DCFDA) staining assay, fluorescein diacetate hydrolysis/propidium iodide staining assay, annexin V/fluorescein isothiocyanate (FITC)/propidium iodide staining assay, flow cytometry, Formazan-based assays (MTT, XTT), green fluorescent protein assay, lactate dehydrogenase (LDH) assay, methyl violet assay, propidium iodide assay, Resazurin assay, trypan blue assay, 4',6'-diamidino-2-phenylindole (DAPI) assay, TUNEL assay, a fluorochrome-labeled inhibitors of caspases (FLICA)-based assay, primary (1°) colonosphere formation assay, thioredoxin reductase assay, 20S proteasome activity assay, and in vitro scratch assay (for cell migration analysis). In a preferred embodiment, the cell viability assay is performed via ATP test using CellTiter-Glo® Luminescent Cell Viability Assay, available from Promega, Madison, Wis., USA.

As used herein, the term "cytotoxic effective amount" refers to a concentration of the active ingredient that reduces the viability of the cancer cells by at least 5%, at least 10%, at least 15%, at least 20%, at least 30%, at least 40%, at least 50%, at least 60%, at least 70%, at least 80% or at least 90%, relative to cancer cells not treated with the active ingredient. The reduction in viability may occur no more than 10 days, no more than 7 days, no more than 5 days, no more than 3 days, or no more than 2 days after the active ingredient is contacted with the cancer cells. In one embodiment, the cytotoxic effective amount may be the $IC_{50}$ which is a concentration of an active ingredient which causes the death of 50% of cellular population of the cancer cells in 6-96 hours, 12-72 hours, or 24-48 hours.

In one embodiment, the $IC_{50}$ of the presently disclosed gold(I) complexes, the salt thereof, the solvate thereof, the tautomer thereof, the stereoisomer thereof, or mixtures thereof against lung cancer cells (e.g. A549) is in a range of 0.1-100 µM, preferably 1-50 µM, more preferably 2-10 µM. In a preferred embodiment, the gold(I) complex is

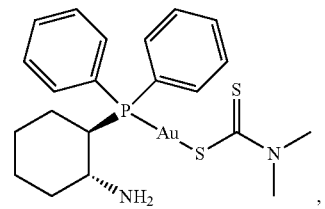

and the $IC_{50}$ against lung cancer cells is about 3.5 µM.

In another embodiment, the $IC_{50}$ of the presently disclosed gold(I) complexes, the salt thereof, the solvate thereof, the tautomer thereof, the stereoisomer thereof, or mixtures thereof against cervical cancer cells (e.g. HeLa) is in a range of 0.1-50 µM, preferably 1-25 µM, more preferably 2-10 µM. In a preferred embodiment, the gold(I) complex is

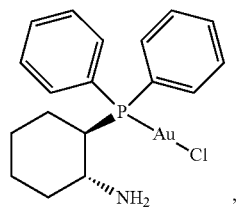

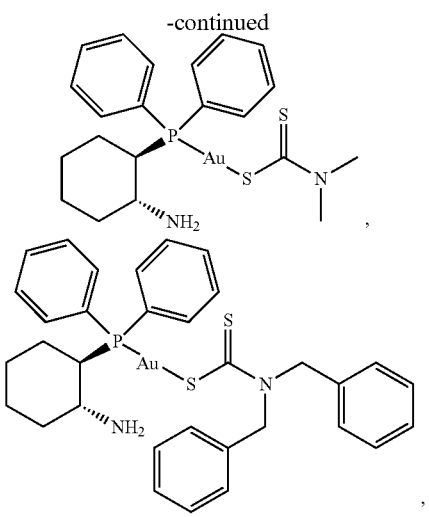

or a mixture thereof, and the $IC_{50}$ against cervical cancer cells is in a range of 0.1-5 µM, preferably 0.5-4 µM, more preferably 2-3 µM.

In another embodiment, the $IC_{50}$ of the presently disclosed gold(I) complexes, the salt thereof, the solvate thereof, the tautomer thereof, the stereoisomer thereof, or mixtures thereof against liver cancer cells (e.g. HepG2) is in a range of 0.1-100 µM, preferably 1-25 µM, more preferably 2-10 µM. In a preferred embodiment, the gold(I) complex is

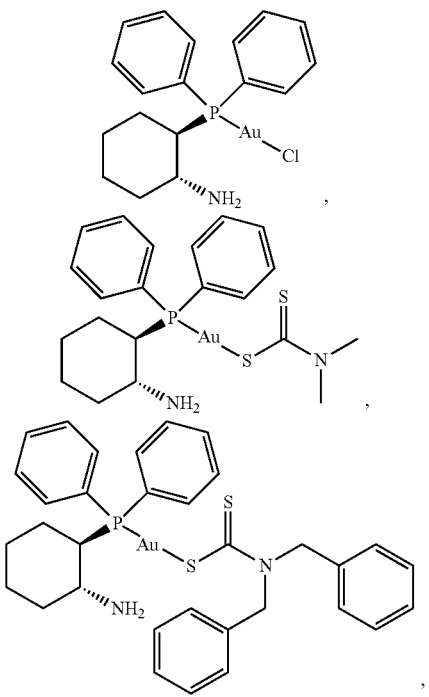

or a mixture thereof, and the $IC_{50}$ against liver cancer cells is in a range of 0.5-7 µM, preferably 2-6 µM, more preferably 3-4 µM.

In some embodiments, other active ingredients in addition to the gold(I) complexes of the current disclosure may be incorporated into the pharmaceutical composition. In one embodiment, the pharmaceutical composition includes an additional active ingredient that is chemically distinct from the gold(I) complex of formula (I), such as a chemotherapeutic agent or an anticancer agent, for the treatment or prevention of neoplasm, of tumor or cancer cell division, growth, proliferation and/or metastasis in the subject; induction of death or apoptosis of tumor and/or cancer cells; and/or any other forms of proliferative disorder.

The additional active ingredient may be an anticancer agent and may include, but is not limited to, at least one of a mitotic inhibitor; an alkylating agent; an antimetabolite; a cell cycle inhibitor; an enzyme; a topoisomerase inhibitor; a biological response modifier; an anti-hormone; a tubulin inhibitor; a tyrosine-kinase inhibitor; an antiangiogenic agent such as MMP-2, MMP-9 and COX-2 inhibitor; an anti-androgen; a platinum coordination complex (cisplatin, oxaliplatin, carboplatin); a substituted urea such as hydroxyurea; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane).

Exemplary anticancer agents include, but are not limited to, tubulin binding agents including paclitaxel, epothilone, docetaxel, discodermolide, etoposide, vinblastine, vincristine, teniposide, vinorelbine, and vindesine; tyrosine-kinase inhibitors including imatinib, nilotinib, dasatinib, bosutinib, ponatinib, and bafetinib; alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; cytotoxic antibiotics including daunorubicin, doxorubicin, idarubicin, mitomycin, actinomycin, epirubicin; topoisomerase inhibitors including irinotecan, mitoxantrone, topotecan, and mixtures thereof.

As used herein, other non-cancerous proliferative disorders that may also be treated by the currently disclosed pharmaceutical composition include, but are not limited to, atherosclerosis, rheumatoid arthritis, psoriasis, idiopathic pulmonary fibrosis, scleroderma, cirrhosis of the liver, lymphoproliferative disorder, other disorders characterized by epidermal cell proliferation such as verruca (warts), and dermatitis. The active ingredient of the current disclosure may also exhibit other therapeutic activities such as antimicrobial (e.g. antibacterial, antifungal, antiviral, antimycobacterial), antimalarial, pesticidal, antioxidant, as well as anti-inflammatory efficacies.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Some examples of physiologically acceptable carriers include antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound. Examples, without limitation, of excipients include calcium carbonate, calcium phosphate, various sugars and types of starch, cellulose derivatives, gelatin, vegetable oils, and polyethylene glycols.

In one or more embodiments, the pharmaceutical composition contains 0.1 to 99.9999 wt. %, preferably 1 to 99.999 wt. %, preferably 5 to 99.99 wt. %, preferably 10 to 99.9 wt. %, preferably 15 to 99 wt. %, preferably 20 to 90 wt. %, preferably 30 to 85 wt. %, preferably 40 to 80 wt. %, preferably 50 to 75 wt. %, preferably 60 to 70 wt. % of the pharmaceutically acceptable carrier and/or excipient relative to a total weight of the pharmaceutical composition.

In one or more embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, but are not limited to, phosphate buffers, citrate buffer, acetate buffers, borate buffers, carbonate buffers, bicarbonate buffers, and buffers with other organic acids and salts.

Exemplary inorganic salts include, but are not limited to, calcium carbonate, calcium phosphate, disodium hydrogen phosphate, potassium hydrogen phosphate, sodium chloride, zinc oxide, zinc sulfate, and magnesium trisilicate.

Exemplary fatty acids include, but are not limited to, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, but are not limited to, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethylammonium bromide, tetradecyltrimethylammonium bromide, tetradecyltrimethyl-ammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the pharmaceutical composition may be in the form of solid dosage form such as tablets, caplets, capsules, powders, and granules, semi-solid dosage form such as ointments, creams, lotions, gels, pastes, and suppositories, liquid dosage forms such as solutions, and dispersions, inhalation dosage form such as aerosols, and spray, or transdermal dosage form such as patches.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavouring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration.

The active ingredient(s) can be dissolved in aqueous or non-aqueous carriers including, but not limited to, water, ethanol, benzyl alcohol, DMSO, polyethylene glycol, propylene glycol, ethanol, corn oil, cottonseed oil, peanut oil, sesame oil, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Formulations of the pharmaceutical compositions of the disclosure for rectal or vaginal administration may be presented as a suppository, which may be prepared by mixing one or more gold(I) complexes with one or more suitable non-irritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active ingredient(s).

Formulations of the pharmaceutical compositions which are suitable for vaginal administration also include pessaries, tampons, creams, gels, pastes, foams or spray formulations containing such carriers as are known in the art to be appropriate.

Topical administration may involve the use of transdermal administration such as transdermal patches or iontophoresis devices. Formulation of drugs is discussed in, for example, Hoover, J. E. Remington's pharmaceutical sciences, Mack Publishing Co., Easton, Pa., 1975; and Liberman, H. A.; Lachman, L., Eds. Pharmaceutical dosage forms, Marcel Decker, New York, N.Y., 1980, which are incorporated herein by reference in their entirety.

In other embodiments, the pharmaceutical composition having the presently disclosed compound(s), the salt thereof, the solvate thereof, the tautomer thereof, the stereoisomer thereof, or the mixture thereof has different release rates categorized as immediate release and controlled- or sustained-release.

As used herein, immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to a release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the pharmaceutical composition described herein is not a controlled-release composition.

According to another aspect, the present disclosure relates to a method for treating a proliferative disorder. The method involves administering a therapeutically effective amount of one or more gold(I) complexes per se, or the pharmaceutical composition described above to a subject in need of therapy.

In one or more embodiments, the proliferative disorder is cancer. Types of cancers that may be treated with the gold(I) complexes of the present disclosure include, but are not limited to, cancers of the blood, stomach, breast, colon, brain, bladder, lung, cervix, ovary, rectum, pancreas, skin, prostate gland, spleen, liver, kidney, head, neck, testicle, bone, bone marrow, thyroid gland, and central nervous system. In some embodiments, the gold(I) complexes of this disclosure can be used for the treatment of any cancer type that fails to undergo apoptosis in a subject. This includes, but is not limited to: solid tumors, including but not limited to carcinomas; sarcomas including Kaposi's sarcoma and osteosarcoma; erythroblastoma; glioblastoma; meningioma; astrocytoma; melanoma; and myoblastoma. Treatment or prevention of non-solid tumor cancers, such as leukemia, is also contemplated by the present disclosure.

Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Bur-kitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse laige B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma. In preferred embodiments, the cancer that may be treated with the gold(I) complexes is lung cancer, cervical cancer, and/or liver cancer.

As used herein, the terms "treat", "treatment", and "treating" in the context of the administration of a therapy to a subject in need thereof refer to the reduction or inhibition of the progression and/or duration of a disease (e.g. cancer), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The term "subject" and "patient" are used interchangeably. As used herein, they refer to any subject for whom or which therapy, including with the compositions according to the present disclosure is desired. In most embodiments, the subject is a mammal, including but not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

As used herein, a subject in need of therapy includes a subject already with the disease, a subject which does not yet experience or exhibit symptoms of the disease, and a subject predisposed to the disease. In preferred embodiments, the subject is a person who is predisposed to cancer, e.g. a person with a family history of cancer. People who (i) smoke or regularly breathe in second-hand smoke, (ii) exposed to carcinogens such as asbestos, radioactive substances (e.g., uranium, radon), and/or (iii) inhaled chemicals or minerals (e.g., arsenic, beryllium, cadmium, silica, vinyl chloride, nickel compounds, chromium compounds, coal products, mustard gas, and chloromethyl ethers) are at a higher risk of contracting lung cancer. People who have been diagnosed with Human papillomavirus (HPV) are at a higher risk of contracting cervical cancer. A person with (i) chronic infection with the hepatitis B virus (HBV) or hepatitis C virus (HCV), (ii) cirrhosis of the liver, (iii) nonalcoholic fatty liver disease, and/or (iv) exposure to aflatoxins is at a higher risk of contracting liver cancer.

In one or more embodiments, the subject refers to a cancer patient who is currently undergoing, or has completed one or more chemotherapy regimens. In some embodiments, the subject has been previously administered/treated with, or is being currently administered/treated with, a thymidylate synthase inhibitor (e.g., capecitabine, fluorouracil (5-FU)), a thymidine phosphorylase (TPase) inhibitor (e.g., tipiracil, trifluridine), a topoisomerase I inhibitor (e.g., irinotecan), a topoisomerase II inhibitor (e.g., doxorubicin), a DNA synthesis inhibitor (e.g., oxaliplatin), a DNA crosslinking agent (e.g., cisplatin), and/or a targeted therapy (e.g., cetuximab, bevacizumab, panitumumab, zivaflibercept, ramucirumab). In preferred embodiments, the subject has been previously administered/treated with, or is being currently administered/treated with, a DNA crosslinking agent (e.g., cisplatin) and developed drug resistance via mechanisms related to decreased intracellular uptake, increased reflux, increased inactivation by sulfhydryl molecules such as glutathione, increased excision of the adducts from DNA by repair pathways, increased lesion bypass, and/or altered expression of regulatory proteins involved in signal transduction pathways that control the apoptotic processes.

In another embodiment, the subject refers to a cancer patient who has been previously administered and/or treated with a platinum-based chemotherapy drug such as Carboplatin, Oxaliplatin, Nedaplatin, Phenanthriplatin, Picoplatin, Satraplatin, Lipoplatin, and cisplatin, and developed resistance to the drug. In some embodiments, the subject refers to a cancer patient who has been previously treated and/or administered with cisplatin and develops cisplatin resistance due to reduced intracellular drug accumulation, overexpression of HER-2/neu and the PI3-K/Akt pathway, increase in DNA damage repair, dysfunction of tumor-suppressor p53, loss of pAMT function, and/or overexpression of antiapoptotic bcl-2. In at least one embodiment, the subject has lung, cervical, and/or cervical cancer and is currently undergoing, or has completed a cisplatin-based chemotherapy regimen.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed with the complexes and methods described herein. In a preferred embodiment, the active ingredient and/or the pharmaceutical composition described herein are administered orally.

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", or "pharmaceutically effective amount" refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. Typically, an effective amount of the gold(I) complex disclosed herein is in a range of 0.01-100 mg/kg, preferably 0.05-90 mg/kg, preferably 0.1-80 mg/kg, preferably 0.5-70 mg/kg, preferably 1-60 mg/kg, preferably 2-50 mg/kg, preferably 3-40 mg/kg, preferably 4-30 mg/kg, preferably 5-20 mg/kg, preferably 6-10 mg/kg, preferably 7-8 mg/kg is administered per body weight of the subject. However, in certain embodiments, the effective amount of the gold(I) complex is less than 0.01 mg/kg or greater than 100 mg/kg.

In treating certain cancers, the best approach is often a combination of surgery, radiotherapy, and/or chemotherapy. Therefore, in at least one embodiment, the pharmaceutical composition is employed in conjunction with radiotherapy. In another embodiment, the pharmaceutical composition is employed with surgery. The radiotherapy and/or surgery may be performed before or after the pharmaceutical composition is administered.

In some embodiments, the gold(I) complexes of the present disclosure are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin ortopotecan; (vii) topoisomerase II poisons, (viii) microtubule-directed agents, (ix) kinase inhibitors (x) miscellaneous investigational agents (xi) hormones, (xii) hormone antagonists, and (xii) targeted therapies. It is contemplated that gold(I) complexes of the disclosure may be useful in combination with any known agents falling into the above 13 classes as well as any future agents that are currently in development. In particular, it is contemplated that gold(I) complexes of the disclosure may be useful in combination with current Standards of Care as well as any that evolve over the foreseeable future. Specific dosages and dosing regimens would be based on physicians' evolving knowledge and the general skill in the art.

Examples of second therapeutic agents include, but are not limited to, a mitotic inhibitor; an alkylating agent; an antimetabolite; a cell cycle inhibitor; an enzyme; a topoisomerase inhibitor; a biological response modifier; an anti-hormone; a tubulin inhibitor; a tyrosine-kinase inhibitor; an antiangiogenic agent such as MMP-2, MMP-9 and COX-2 inhibitor; an anti-androgen; a platinum coordination complex (oxaliplatin, carboplatin, cisplatin); a substituted urea such as hydroxyurea; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane); a thymidylate synthase inhibitor; a thymidine phosphorylase (TPase) inhibitor; a DNA synthesis inhibitor; and/or a targeted therapy. Exemplary second therapeutic agents include, but are not limited to, tubulin binding agents including paclitaxel, epothilone, docetaxel, discodermolide, etoposide, vinblastine, vincristine, teniposide, vinorelbine, and vindesine; tyrosine-kinase inhibitors including imatinib, nilotinib, dasatinib, bosutinib, ponatinib, and bafetinib; alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; cytotoxic antibiotics including daunorubicin, doxorubicin, idarubicin, mitomycin, actinomycin, epirubicin; topoisomerase inhibitors including irinotecan, mitoxantrone, topotecan; thymidine phosphorylase (TPase) inhibitors such as tipiracil and trifluridine; DNA synthesis inhibitors such as oxaliplatin; targeted therapies such as cetuximab, bevacizumab, panitumumab, zivaflibercept, ramucirumab; and mixtures thereof.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intratumoral routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Any other administration route combination is also contemplated herein according to the administration routes available for each of the therapeutic agents. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

A treatment method may comprise administering a pharmaceutical composition containing the gold(I) complex of the current disclosure in any of its embodiments as a single dose or multiple individual divided doses. In some embodiments, the composition is administered at various dosages (e.g. a first dose with an effective amount of 50 mg/kg and a second dose with an effective amount of 10 mg/kg). In some embodiments, the interval of time between the administration of the composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, at least 5 days, at least 6 days, or at least 7 days. In certain embodiments, the composition and one or more additional therapies are administered less than 1 day, less than 1 week, less than 2 weeks, less than 3 weeks, less than 4 weeks, less than 1 month, less than 2 months, less than 3 months, less than 6 months, less than 1 year, less than 2 years, or less than 5 years apart.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, at least 10%, at least 15%, at least 20%, at least 25%, at least 30%, at least 40%, at least 50%, at least 60%, at least 70%, at least 75%, at least 80%, at least 85%, at least 90%, at least 95%, at least 99%, or 100%, relative to the tumor size before treatment. In other embodiments, the size of a tumor after treatment does not reduce but is maintained the same as the tumor size before treatment. Methods of assessing tumor size include, but are not limited to, CT scan, MRI, DCE-MRI, PET scan, and manual tumor measurement.

In most embodiments, the method further involves measuring a concentration of a biomarker and/or detecting a mutation in a biomarker before and/or after the pharmaceutical composition comprising the compound of the present disclosure is administered. As used herein, the term "biomarker" refers to a characteristic that is objectively measured and evaluated as an indicator of normal biological processes, pathogenic processes or pharmacological responses to a therapeutic intervention. Generic cancer biomarkers include circulating tumor DNA (ctDNA) and circulating tumor cells (CTC). Exemplary biomarkers for lung cancer include, without limitation, CYFRA 21-1 (cytokeratins), EPCAM (epithelial cell adhesion molecule), ProGRP (pro-gastrin-releasing peptide), and CEACAM (carcinoembryonic antigen). Exemplary biomarkers for cervical cancer include, without limitation HPV E6, HPV E7, Mini chromosome maintenance (MCM), Cell division cycle protein 6 (CDC6), $p16^{INK4A}$, Squamous cell carcinoma antigen (SCC), and Ki-67. Exemplary biomarkers for liver cancer include, without limitation, alpha-fetoprotein (AFP), AFP-L3, des-γ-carboxyprothrombin (DCP), GPC3, GP73, cytokeratin 19 (CK 19), osteopontin, IL-6, midkine (MDK), and Annexin A2.

The mutation in the biomarker may be detected by procedures such as restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA). The procedures to detect the mutation are well-known to those of ordinary skill in the art.

The term "sample" used herein refers to any biological sample obtained from the subject in need of therapy including a single cell, multiple cells, fragments of cells, a tissue sample, and/or body fluid. Specifically, the biological sample may include red blood cells, white blood cells, platelets, hepatocytes, epithelial cells, endothelial cells, a skin biopsy, a mucosa biopsy, an aliquot of urine, saliva, whole blood, serum, plasma, lymph. In some embodiments, the biological sample is taken from a tumor.

The concentration level of the cancer biomarker in a sample may be measured by an assay, for example an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

In some embodiments, a concentration of the biomarker is measured before and after the administration. When the concentration of the biomarker is maintained, the method may further comprise increasing the effective amount of the compound of the present disclosure by at least 5%, at least 10%, or at least 30%, up to 50%, up to 60%, or up to 80% of an initial effective amount The subject may be administered with the increased dosage for a longer period (e.g. 1 week more, 2 weeks more, or 2 months more) than the duration prescribed with the initial effective amount.

In some embodiments, the mutation in the biomarker is detected before administering the composition to identify subjects predisposed to the disease. Alternatively, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

The examples below are intended to further illustrate protocols for preparing, characterizing, and using the gold(I) complexes of the present disclosure, and are not intended to limit the scope of the claims.

Example 1

Materials

Sodium tetrachloridoaurate(III) dihydrate (NaAuCl$_4$.2H$_2$O), sodium salts of dimethyldithiocarbamate dihydrate, diethyldithiocarbamate, and dibenzyldithiocarbamate, ethanol, acetone, and dichloromethane were purchased from Sigma Aldrich, Co. United States. (1R,2R)-2-(diphenylphosphino)-1-aminocyclohexane (ACP) was purchased from Strem Chemicals Inc. Massachusetts, United States. Dimethylsulfide was provided by Fluka AG, St. Gallen, Switzerland. All solvents are of analytical grade and were used without further purification.

Example 2

Instrumentation

Elemental analysis was obtained on Perkin Elmer Series 11 (CHNS/O), Analyzer 2400. Solid-state FTIR spectra of the free ligands and their gold(I) complexes were recorded on a Perkin Elmer FTIR 180 spectrophotometer over the range of 4000-400 cm$^{-1}$ at a resolution of 4.0 cm$^{-1}$. $^1$H, $^{13}$C, and $^{31}$P NMR spectra were recorded on a JEOL-LA 500 NMR spectrophotometer, operating at 500.0, 125.65, and 200.0 MHz respectively, corresponding to a magnetic field of 11.74 T. The $^{13}$C NMR spectra were obtained using $^1$H broadband decoupling with following spectral conditions: 32 k data points, 1 s acquisition time, 2.5 s pulse delay, and 5.12 μs pulse width. All spectra were recorded at 297 K in CDCl$_3$. For $^1$H and $^{13}$C NMR, tetramethylsilane (TMS) was used as an internal standard, while the $^{31}$P NMR chemical shifts were recorded relative to an external reference (H$_3$PO$_4$ in D$_2$O) at 0.00 ppm.

Example 3

Synthesis of Gold(I) Complexes 1-4: Experimental

The parent compound, (CH$_3$)$_2$S—AuCl was prepared by a method similar to one reported previously [S. Ahmad, M. N. Akhtar, A. A. Isab, A. R. Al-Arfaj, M. S. Hussain, J. Coord. Chem. 51 (2000) 225-234, incorporated herein by reference in its entirety]. The white product obtained was washed twice with ethanol (5.0 mL), and three times with diethyl ether (10 mL), then dried in the dark and stored in fridge. (Yield=91%). Calc. for C$_2$H$_6$AuClS=294.55 g/mol: C, 8.35; H, 2.13. Found: C, 8.12; H, 1.83. $^1$H NMR (CDCl$_3$, ppm), δ 2.75 (s, 6H). $^{13}$C NMR (CDCl$_3$, ppm) δ 25.3.

Gold(I) complex 1 was synthesized by adding 0.5 mmol of 2-(diphenylphosphanyl)-1-aminocyclohexane (ACP) in 10 mL dichloromethane dropwise to a solution of 0.5 mmol of (CH$_3$)$_2$S—AuCl in 5.0 mL of dichloromethane. The mixing resulted in a colorless solution that was stirred for 30 min. The solvent was then concentrated by slow evaporation at room temperature. The crude product was obtained as a white solid, which was then recrystallized from dichloromethane/ethanol mixture and dried under vacuum overnight. (Yield=87%).

Analysis of gold(I) complex 1: Calc. for 1, C$_{18}$H$_{22}$NPAuCl (515.77 g/mol): C, 41.91; H, 4.30; N, 2.72. Found: C, 41.17; H, 3.85; N, 2.34. IR (cm$^{-1}$) ν(N—H) 3461, 3324; ν(CH$_2$) 2935$_{asym}$, 2850$_{sym}$, ν(C—H) 1315$_{bend}$, δ(N—H) 1572, ν(P—C) 1242. $^1$H NMR (CDCl$_3$, ppm) δ 1.97 (s, NH), 2.54 (m, C(1)H), 3.15 (m, C(2)H), 1.74 (m, C(3)H), 1.33 (m, C(4)H), 1.22 (m, C(5)H), 1.42 (m, C(6)H), 7.47-7.94 (m, 10H, C$_6$H$_5$). $^{13}$C NMR (CDCl$_3$, ppm) δ 43.54C(1), 56.01C(2), 37.65C(3), 25.65C(4), 24.73C(5), 28.10C(6), 128.96-134.84C(C$_6$H$_5$). $^{31}$P NMR (CDCl$_3$, ppm) δ 41.84.

For gold(I) complexes 2-4, to a stirred solution having a 1:1 mixture of (CH$_3$)$_2$S—AuCl and phosphane (ACP) in 15 mL dichloromethane, the corresponding sodium dithiocarbamate ligand (0.5 mmol) in 10 mL ethanol was added dropwise with continuous stirring for 2 h at room temperature. The mixture was then filtered, and the clear colored solution was kept at room temperature for slow evaporation. The yellow or orange solids obtained were recrystallized from acetone/dichloromethane and dried under vacuum overnight. (Yield=85-88%).

Analysis of gold(I) complex 2: Calc. for 2, C$_{20}$H$_{28}$AuN$_2$PS$_2$ (600.53 g/mol): C, 42.00; H, 4.69; N, 4.66; S, 10.67. Found: C, 41.64; H, 4.77; N, 4.40; S, 10.40. IR (cm$^{-1}$) ν(N—H) 3461, 3334; ν(CH$_2$) 2927$_{asym}$, 2851$_{sym}$, ν(C—H) 1246$_{bend}$, δ(N—H) 1615, ν(C—N) 1486, ν(C=S) & ν(P—C) 1134, 1099. $^1$H NMR (CDCl$_3$, ppm) δ 1.92 (s, NH), 3.35 (m, C(1)H), 3.38 (m, C(2)H), 1.87 (m, C(3)H), 1.30 (m, C(4)H), 1.29 (m, C(5)H), 1.45 (m, C(6)H), 3.52 (m, C(8)H), 7.47-8.06 (m, 10H, C$_6$H$_5$). $^{13}$C NMR (CDCl$_3$, ppm) δ 45.29C(1), 54.55C(2), 40.96C(3), 25.18C(4), 24.04C(5), 30.92C(6), 207.51C=S(7), 50.53C(8), 128.97-134.05C (C$_6$H$_5$). $^{31}$P NMR (CDCl$_3$, ppm) δ 41.68.

Analysis of gold(I) complex 3: Calc. for 3, C$_{23}$H$_{32}$AuN$_2$PCS$_2$ (640.59 g/mol): C, 44.99; H, 5.03; N, 4.37; S, 10.01. Found: C, 44.64; H, 4.77; N, 4.40; S, 10.40. IR (cm$^{-1}$) ν(N—H) 3461, 3334; ν(CH$_2$) 2927$_{asym}$, 2851$_{sym}$, ν(C—H) 1264$_{bend}$, δ(N—H) 1610, ν(C—N) 1496, ν(C=S) & ν(P—C) 1068, 984. $^{1H}$ NMR (CDCl$_3$, ppm) δ 1.93 (s, NH), 2.93 (m, C(1)H), 3.46 (m, C(2)H), 2.32 (m, C(3)H), 1.35 (m, C(4)H), 1.41 (m, C(5)H), 1.83 (m, C(6)H), 3.54 (s, C(8)H), 1.33 (s, C(9)H) 7.46-8.12 (m, 10H, C$_6$H$_5$). $^{13}$C NMR (CDCl$_3$, ppm) δ 44.12C(1), 54.87C(2), 39.55C(3), 25.11C(4), 24.15C(5), 29.65C(6), 204.16C=S(7), 52.25C(8), 12.1C(9), 128.38-134.65C(C$_6$H$_5$). $^{31}$P NMR (CDCl$_3$, ppm) δ 40.15.

Analysis of gold(I) complex 4: Calc. for 4, C$_{33}$H$_{36}$AuN$_2$PS$_2$ (752.72 g/mol): C, 52.65; H, 4.82; N, 3.72; S, 8.51. Found: C, 52.04; H, 4.25; N, 3.81; S, 8.06. IR (cm$^{-1}$) ν(N—H) 3461, 3334; ν(CH$_2$) 2923$_{asym}$, 2852$_{sym}$, ν(C—H) 1210$_{bend}$, δ(N—H) 1600, ν(C—N) 1437, ν(C=S) & ν(P—C) 1099, 973. $^1$H NMR (CDCl$_3$, ppm) δ 1.7 (s, NH), 3.25 (m, C(1)H), 3.88 (m, C(2)H), 2.02 (m, C(3)H), 0.88 (m, C(4)H), 1.46 (m, C(5)H), 1.84 (m, C(6)H), 4.71, 5.11 (d, C(8)H), 7.48-8.11 (m, 20H, C$_6$H$_5$). $^{13}$C NMR (CDCl$_3$, ppm) δ 43.65C(1), 55.88C(2), 37.06C(3), 25.74C(4), 24.45C(5), 27.89C(6), 210.17C=S(7), 58.40C(8), 127.82-135.92C (C$_6$H$_5$). $^{31}$P NMR (CDCl$_3$, ppm) δ 39.18.

Example 4

Synthesis of Gold(I) Complexes 1-4: Results and Discussion

The reaction of 2-(diphenylphosphanyl)-1-aminocyclohexane (ACP) with (CH$_3$)$_2$S—AuCl in 1:1 molar ratio yielded gold(I) complex 1 [Au(ACP)Cl] as colorless crystals. The mixed ligand gold(I) complexes 2-4 were prepared by addition of one equivalent of a dithiocarbamate ligand to a 1:1 mixture of (CH$_3$)$_2$S—AuCl and the phosphane. The products obtained have the composition [Au(phosphane)(dithiocarbamate)] as indicated by the elemental analysis. The structure of complex 1 was established by single crystal X-ray diffraction. Gold(I) complexes 2-4 may be mononuclear molecules possessing a linear geometry at the gold center [F. K. Keter, I. A. Guzei, M. Nell, W. E. van Zyl, J. Darkwa, Inorg. Chem. 2014, 53, 2058-2067; V. Gandin, A. P. Fernandes, M. P. Rigobello, B. Dani, F. Sorrentino, F. Tisato, M. Bjornstedt, A. Bindoli, A. Sturaro, R. Rella and C. Marzano, Biochem. Pharmacol., 2010, 79, 90-101; D. de Vos, S. Y. Ho, E. R. T. Tiekink, Bioinorg. Chem. Appl. 2004, 2, 141-154; M. Altaf, M. Monim-ul-Mehboob, A. A. A. Seliman, M. Sohail, M. I. M. Wazeer, A. A. Isab, L. Li, V. Dhuna, G. Bhatia, K. Dhuna, Eur. J. Med. Chem. 95 (2015) 464-472; and S. S. Al-Jaroudi, M. Altaf, A. A. Seliman, S. Yadav, F. Arjmand, A. Alhoshani, H. M. Korashy, S. Ahmad, A. A. Isab, Inorg. Chim. Acta, 464 (2017) 37-48, each incorporated herein by reference in their entirety]. The procedure for synthesis of these complexes is illustrated in FIG. 2.

Selected IR frequencies of the synthesized gold(I) complexes are given in experimental section. In the IR spectra of all gold(I) complexes 1-4, the N—H stretching bands of amino group of phosphane were observed at around 3400 and 3340 cm$^{-1}$, respectively. The —NH$_2$ bending vibrations were detected at about 1600 cm$^{-1}$. The ν(P—C) band of ACP [A. A. Isab, S. Nawaz, M. Saleem, M. Altaf, M. Monim-ul-Mehboob, S. Ahmad, H. Stoeckli-Evans, Polyhedron 29 (2010) 12, incorporated herein by reference in its entirety] and the band due to the —C=S moiety of dithiocarbamates [A. A. Isab, S. Nawaz, M. Saleem, M. Altaf, M. Monim-ul-Mehboob, S. Ahmad, H. Stoeckli-Evans, Polyhedron 29 (2010) 12, incorporated herein by reference in its entirety] were observed to be overlapping, and appeared as a single peak at around 1100 cm$^{-1}$. The C—N stretching vibration of the dithiocarbamate (N—CSS$^-$) group was observed near 1500 cm$^{-1}$ [M. Altaf, M. Monim-ul-Mehboob, A. A. Seliman, M. Sohail, M. I. M. Wazeer, A. A. Isab, L. Li, V. Dhuna, G. Bhatia, K. Dhuna, Eur. J. Med. Chem. 95 (2015) 464-472; S. S. Al-Jaroudi, M. Altaf, A. A. Seliman, S. Yadav, F. Arjmand, A. Alhoshani, H. M. Korashy, S. Ahmad, A. A. Isab, Inorg. Chim. Acta, 464 (2017) 37-48; and A. A. Sulaiman, M. Altaf, A. A. Isab, A. Alawad, S. Altuwaijri, S. Ahmad, Z. Anorg. Allg. Chem., 642 (2016) 1454-1459, each incorporated herein by reference in their entirety]. This value defines an intermediate carbon-nitrogen bond order between a single bond (ν=1350-1250 cm$^{-1}$) and a double bond (ν=1690-1640 cm$^{-1}$) [M. Sarwar, S. Ahmad, S. Ahmed, S. Ali, S. A. Awan, 32 (2007) 199-203, incorporated herein by reference in its entirety]. The aromatic and aliphatic C—H stretching bands of medium intensity bands were observed in the regions of 3000 and 2900 cm$^{-1}$, respectively.

As shown in the $^1$H NMR spectra of the complexes, the hydrogens of —CH group attached to nitrogen and phosphorus atoms resonate at around 2.5-3 and about 3 ppm, respectively. The diastereotopic benzylic methylene protons in gold(I) complex 4 had two signals at 4.7 and 5.1 ppm. Other aliphatic protons appeared as multiplets between 1-2 ppm. The aromatic hydrogens were observed between 7-8 ppm. In the $^{13}$C NMR spectra of these complexes, the carbon atoms attached to phosphorus appeared as doublets due to coupling with $^{31}$P nuclei. The C=S resonances of dithiocarbamates were observed at the most downfield position at above 200 ppm. The appearance of this peak indicates the complexation of dithiocarbamates to gold(I). The next upfield resonances were assigned to the alkyl carbons attached to the dithiocarbamate moiety. The remaining methyl or methylene moieties were detected between 10-30 ppm. The aromatic signals of ACP phosphane and dibenzyl groups were observed in the region of 120-135 ppm. The $^{31}$P NMR chemical shifts for gold(I) complexes 1-4 were observed near 40 ppm.

Example 5

Determination of Single Crystal Structure

Suitable crystals of gold(I) complex 1 were obtained as colorless rods from dichloromethane/ethanol mixture. The X-ray data were collected at 173 K on a Stoe IPSD 2 Image Plate Diffraction System [Stoe & Cie., *X-Area X-RED*32, *Stoe Cie GmbH*, Darmstadt, Germany 2009] connected with a two-circle goniometer and using MoKα graphite monochromator (λ=0.71073 Å). The structure was solved by SHELXS-2014 program [G. M. Sheldrick, "A short history of SHELX.," Acta Crystallogr. A., vol. 64 (2008) 112-22]. The refinement and further calculations were carried out with SHELXL-2014 [G. M. Sheldrick, "A short history of SHELX.," Acta Crystallogr. A., vol. 64 (2008) 112-22]. A semi-empirical absorption correction was applied using the MUL scan ABS routine in PLATON [A. L. Spek, "Structure validation in chemical crystallography," Acta Crystallogr. Sect. D Biol. Crystallogr., vol. 65 (2009) 148-155]. The crystal structure and crystal packing were drawn using Mercury software [J. van de S. and P. A. W. C. F. Macrae, I. J. Bruno, J. A. Chisholm, P. R. Edgington, P. McCabe, E. Pidcock, L. Rodriguez-Monge, R. Taylor, J. Appl. Cryst., vol. 41 (2008) 466-470]. The crystal data and refinement details are given in Table 1. Crystallographic data of the complex have been deposited with the Cambridge Crystallographic Data Center via the CCDC Numbers 1960931. Copies of the data can be obtained free of charge on application to CCDC, 12 Union Road, Cambridge CB2 1EZ, UK, e-mail: deposit@ccdc.cam.ac.uk or www.ccdc.cam.ac.uk.

TABLE 1

Summary of crystal data and details of the structure refinement for gold (I) complex 1

| Parameter | Details |
|---|---|
| Formula | $C_{18}H_{22}NPAuCl$ |
| Formula weight | 515.75 |
| Crystal symmetry | Monoclinic |
| Space group | P 2$_1$ |
| a, b, c (Å) | 9.5364 (5), 17.3845 (11), 10.9433 (5) |
| α, β, γ (°) | 90, 91.417 (4), 90 |
| Cell volume (Å$^3$) | 1813.69 (17) |
| Z | 4 |
| ρ$_{calc}$ (g cm$^{-3}$) | 1.892 |
| μ (mm$^{-1}$) | 8.34 |
| F (000) | 996 |
| Crystal size (mm) | 0.45 × 0.30 × 0.15 |
| Temperature (K.) | 173 |
| λ Mo Kα (Å) | 0.71073 |
| θ values (°) | θ$_{max}$ = 25.7, θ$_{min}$ = 1.9 |
| h, k, l limits | h = −11→11, k = −21→21, l = −13→13 |
| Reflections: total/unique/Rint | 22693, 6857, 5826/0.061 |
| T$_{min}$, T$_{max}$ | 0.386, 1.000 |
| R[F$^2$ > 2σ (F$^2$)], wR(F$^2$), S | 0.025, 0.052, 0.90 |
| Largest diff. Peak, hole (e Å$^{-3}$) | 1.21, −0.95 |

Example 6

X-Ray Structure of Gold(I) Complex 1

Figure 3:
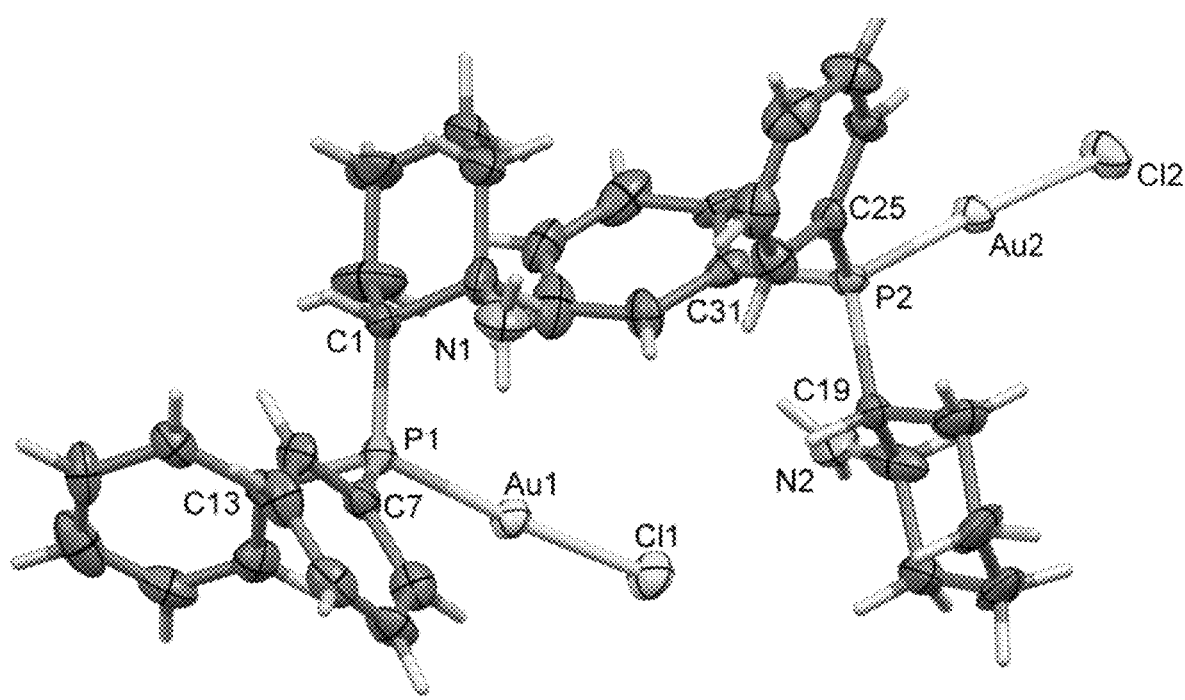
FIG. 3 is ORTEP drawing (30% probability ellipsoids) of the crystal structure of gold(I) complex 1.

The molecular structure of gold(I) complex 1 [Au($C_{18}H_{22}NP$)Cl] is depicted in FIG. 3. Selected bond lengths and bond angles are summarized in Table 2.

TABLE 2

Selected bond lengths and bond angles of gold (I) complex 1

| Bond Lengths (Å) | | Bond Angles (°) | |
| --- | --- | --- | --- |
| Au1—Cl1 | 2.297 (5) | P1—Au1—Cl1 | 176.93 (17) |
| Au1—P1 | 2.243 (4) | Au1—P1—C1 | 110.5 (5) |
| P1—C1 | 1.825 (16) | Au1—P1—C7 | 114.0 (5) |
| P1—C7 | 1.817 (13) | Au1—P1—C13 | 113.2 (5) |
| P1—C13 | 1.812 (12) | C1—P1—C7 | 109.6 (7) |
| C2—N1 | 1.413 (17) | C1—P1—C13 | 106.0 (6) |
| | | C7—P1—C13 | 103.0 (6) |

Gold(I) complex 1 exists as discrete monomeric molecules. The Au(I) atom in gold(I) complex 1 is almost linearly coordinated to the phosphorous atom of a phosphane molecule and a Cl$^-$ ion with ∠P1-Au—Cl1 angle of 176.93 (17)°. The single crystal structure analysis of a $Cy_3P$ (Cy=cyclohexyl) complex, [$Cy_3P$—Au-(thiourea)]Cl [A. A. Isab, M. B. Fettouhi, S. Ahmad, L. Ouahab, 22 (2003) 1349-1354, incorporated herein by reference in its entirety] revealed that the geometry at gold(I) deviated significantly from linearity with a P—Au—S bond angle of 168.54(9). The deviation from linearity was ascribed to the intramolecular Au . . . $NH_2$(thiourea) contact at a distance of 3.418(3) Å. No such contact of Au(I) with $NH_2$ group was observed in the case of gold(I) complex 1. The phosphane ligand binds only through phosphorus, while —$NH_2$ group remains uncoordinated. The amino cyclohexane group adopts a chair conformation. The tertiary phosphine has a common propeller-type arrangement characteristic for this type of ligands [D. Schneider, S. Nogai, A. Schier, H. Schmidbaur, Inorg. Chim. Acta 352 (2003) 179-187, incorporated herein by reference in its entirety]. The phosphorus atom in the complex has a usual tetrahedral environment. The Au1-P1 and Au1-Cl1 bond distances are 2.243 (4) and 2.297 (5) Å respectively, and fall within the range of other chloridophosphane gold(I) complexes [N. C. Baenziger, W. E. Bennett, D. M. Soborofe, Acta Cryst B. 32 (1976) 962; and K. Angermaier, E. Zeller, H. Schmidbaur, J. Organomet. Chem. 472 (1994) 371-376, each incorporated herein by reference in their entirety], such as $Ph_3P$—AuCl (2.235(3) and 2.279(3) Å) [N. C. Baenziger, W. E. Bennett, D. M. Soborofe, Acta Cryst B. 32 (1976) 962, incorporated herein by reference in its entirety]. However, the Au—P bond is particularly short when compared with some other phosphanegold(I) complexes [D. Schneider, S. Nogai, A. Schier, H. Schmidbaur, Inorg. Chim. Acta 352 (2003) 179-187; S. Ahmad, Coord. Chem. Rev. 248 (2004) 231-243; P. G. Jones, J. Launter, Acta Crystallogr. C 44 (1988) 2091; A. R. Al-Arfaj, J. H. Reibenspies, M. S. Hussain, M. Y. Darensbourg, N. Akhtar, A. A. Isab, Acta Crystallogr., Sect. C 53 (1997) 1553; and M. Dennehy, O. V. Quinzani, R. M. Ferullo, A. Granados, R. A. Burrow, Inorg. Chim. Acta 377 (2011) 77-83, each incorporated herein by reference in their entirety]. For example, the Au—P bond has a length of 2.2542(13) Å in [$Ph_3P$—Au—SCN] [D. Schneider, S. Nogai, A. Schier, H. Schmidbaur, Inorg. Chim. Acta 352 (2003) 179-187, incorporated herein by reference in its entirety], 2.278 Å in [$Ph_3P$—Au—CN] [P. G. Jones, J. Launter, Acta Crystallogr. C 44 (1988) 2091, incorporated herein by reference in its entirety], 2.287(3) Å in [$Cy_3P$—Au—CN] [A. R. Al-Arfaj, J. H. Reibenspies, M. S. Hussain, M. Y. Darensbourg, N. Akhtar, A. A. Isab, Acta Crystallogr., Sect. C 53 (1997) 1553, incorporated herein by reference in its entirety], 2.2533(6) Å in [$Ph_3P$—Au-(indazolyldithiocarbamate)] [F. K. Keter, I. A. Guzei, M. Nell, W. E. van Zyl, J. Darkwa, Inorg. Chem. 2014, 53, 2058-2067, incorporated herein by reference in its entirety], 2.2623(9) Å in [$Ph_3P$—Au-(thiosaccharinate)] [M. Dennehy, O. V. Quinzani, R. M. Ferullo, A. Granados, R. A. Burrow, Inorg. Chim. Acta 377 (2011) 77-83, incorporated herein by reference in its entirety], and 2.274(2) Å in [$Cy_3P$—Au-(thiourea)]Cl [A. A. Isab, M. B. Fettouhi, S. Ahmad, L. Ouahab, 22 (2003) 1349-1354, incorporated herein by reference in its entirety]. A shorter distance indicates a greater donation of electron density by the phosphane due to the presence of an amino group. As shown in [TPA-Au-(2-pyridylbenzimidazolate)] (TPA=1,3,5-triaza-7-phosphaadamantane), where the phosphane contains three nitrogen atoms, the Au—P distance is even shorter (2.205(4) Å) [M. Serratrice, M. A. Cinellu, L. Maiore, M. Pilo, A. Zucca, C. Gabbiani, A. Guerri, I. Landini, S. Nobili, E. Mini, L. Messori, Inorg. Chem. 2012, 51, 3161-3171, incorporated herein by reference in its entirety]. The structure of complex 1 is comparable to some phosphanegold(I)-chloride complexes [K. Angermaier, E. Zeller, H. Schmidbaur, J. Organomet. Chem. 472 (1994) 371-376, incorporated herein by reference in its entirety]. Intermolecular hydrogen bonds in gold(I) complex 1 are observed between —$NH_2$ group of phosphane and Cl$^-$ ions of neighboring molecular species.

Example 7

Anti-Proliferative Study

The cell growth inhibition effects of gold(I) complexes 1-4 and cisplatin were measured by the Cell Titer-Glo® luminescence-based assay against the A549 (human lung carcinoma), HeLa (human cervical cancer), and HepG2 (human liver cancer) cell lines according to manufacturer's protocol. Briefly, the cell suspensions were added to each well of 384-w plate at a suitable density (total volume of 40 μL). The margin wells of plate were filled with PBS buffer. The gold(I) complexes were added at various concentrations in triplicate (10 μL solutions of the complex added to the plate), then the plate was incubated for 72 hours in 5% $CO_2$ incubator at 37° C. After that the Cell Titer reagent was added to each tested well and stirred for 2 minutes on an orbital shaker. The plate was shortly centrifuged for 30 seconds and incubated at room temperature for additional 10 minutes to stabilize the luminescent signal. Luminescence signals were measured on PHERAstar Plus. Data acquisition and analysis were performed using Microsoft Excel (version 2003) program and GraphPad Prism 6. The potential effect of the testing complexes on cell growth inhibition expressed as $IC_{50}$ values was calculated by the formula below:

Cell growth Inhibition %=100-100*(Luminescence$_{complex}$)/(Luminescence$_{DMSO}$)

Cell viability %=100*(Luminescence$_{complex}$)/(Luminescence$_{DMSO}$)

Example 8

Cytotoxic Activity of the Gold(I) Complexes

Figure 4:
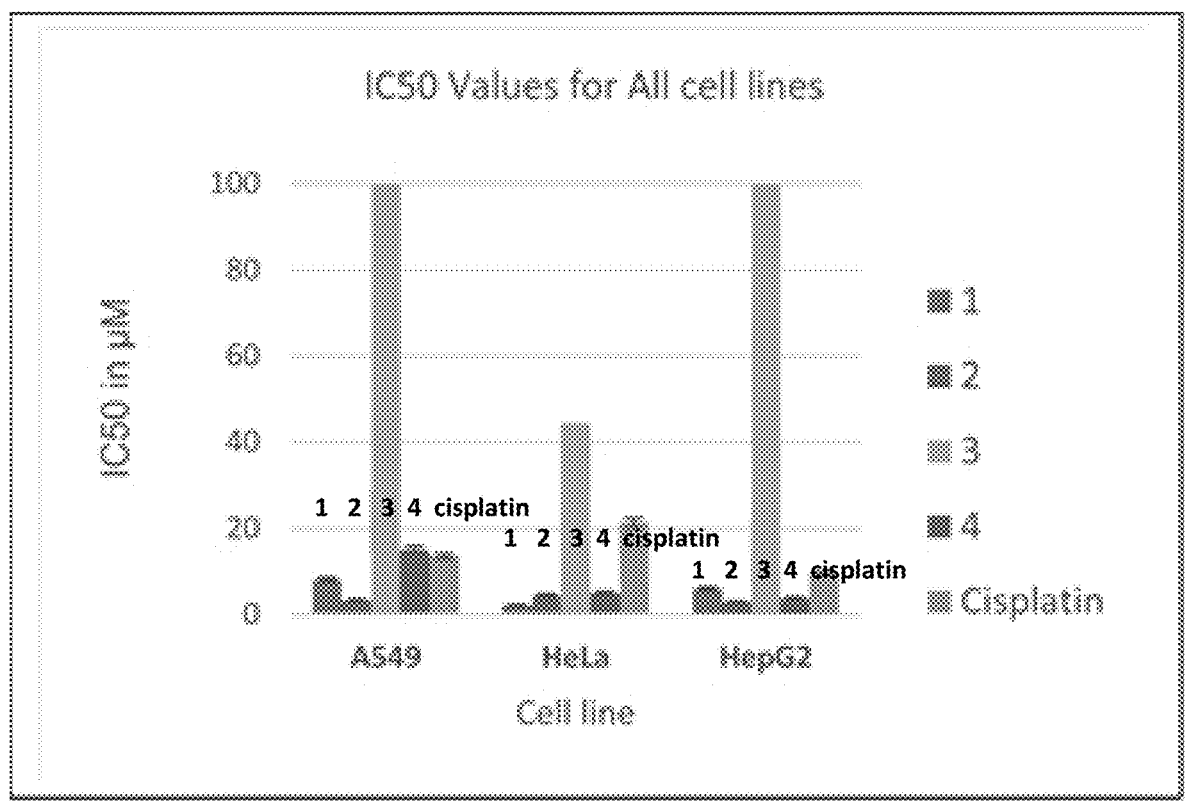
FIG. 4 is a bar graph showing the concentration dependent cytotoxicity of gold(I) complexes 1-4 and cisplatin on the viability of A549, HeLa, and HepG2 cancer cells, respectively.

The gold(I) complexes 1-4 and cisplatin were examined for their cell growth inhibition effects against A549, HeLa, and HepG2 human cancer cell lines using Cell Titer-Glo® luminescence-based assay. The dose-dependent inhibition of cell proliferation was obtained by specific increase of the complex concentrations against a fixed number of each cell line as shown in FIG. 4. The $IC_{50}$ values (see Table 3) were obtained by plotting the complex concentrations against the percentage of cell viability.

TABLE 3

Half-maximal inhibitory concentrations ($IC_{50}$) values (μM) of gold(I) complexes and cisplatin in A549, HeLa, and HepG2 cancer cell lines

| Compound | $IC_{50}$ values (μM) | | |
|---|---|---|---|
| | A549 | HeLa | HepG2 |
| 1 | 8.26 (0.52) | 2.21 (0.25) | 6.19 (0.15) |
| 2 | 3.50 (0.53) | 4.6 (0.20) | 3.11 (0.13) |
| 3 | >100 | 44.5 (0.27) | >100 |
| 4 | 15.30 (0.40) | 5.14 (0.11) | 4.06 (0.08) |
| Cisplatin | 13.75 (0.4) | 21.39 (0.726) | 9.6 (0.9) |

The $IC_{50}$ values for the complexes were in range of 2.2 μM to >100 μM. The data clearly show that gold(I) complexes 1, 2, and 4 have excellent inhibition of cell proliferation, and gold(I) complex 2 demonstrates the best inhibition among the three. Their $IC_{50}$ values are 6-46-fold better than those of cisplatin. Gold(I) complex 3 shows moderate inhibition activity with respect to cisplatin. Specifically, the effectiveness for HeLa cells of gold(I) complex 3 is greater than cisplatin. The higher potency of the inhibition of cell proliferation of the presently disclosed gold(I) complexes can be related to the presence of the labile phosphane and dithiocarbamate ligands bond to gold(I) ion, which may enhance the activity and selectivity of the complexes [K. K. Ooi, C. I. Yeo, K.-P. Ang, A. M. Akim, Y.-K. Cheah, S. N. A. Halim, H.-L. Seng, and E. R. T. Tiekink, J. Biol. Inorg. Chem., 20 (2015) 855-873, incorporated herein by reference in its entirety]. The cytotoxicity profile of the complexes is comparable to some alkylphosphane gold(I) dithiocarbamates [M. Altaf, M. Monim-ul-Mehboob, A. A. A. Seliman, M. Sohail, M. I. M. Wazeer, A. A. Isab, L. Li, V. Dhuna, G. Bhatia, K. Dhuna, Eur. J. Med. Chem. 95 (2015) 464-472; and S. S. Al-Jaroudi, M. Altaf, A. A. Seliman, S. Yadav, F. Arjmand, A. Alhoshani, H. M. Korashy, S. Ahmad, A. A. Isab, Inorg. Chim. Acta, 464 (2017) 37-48, each incorporated herein by reference in their entirety].

Example 9

The present disclosure describes the synthesis and spectroscopic characterization of gold(I) complexes having a phosphane ligand (e.g., 2-(diphenylphosphanyl)-1-aminocyclohexane (ACP)) and dithiocarbamates as well as their antiproliferative activity against A549, HeLa, and HepG2 human cancer cell lines. The structure of gold(I) complex 1 [Au(ACP)Cl] was determined by X-ray crystallography, which revealed that the complex is mononuclear exhibiting a linear geometry along the gold(I) center. It has been observed that these gold complexes are extremely effective in inhibiting the growth of all three types of cell lines. The significant cytotoxicity of the gold(I) complexes disclosed herein demonstrate their potential as effective anticancer agents.

The invention claimed is:

1. A gold(I) complex of formula (I)

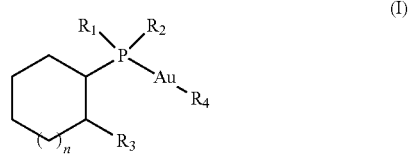

or a salt thereof, a solvate thereof, a tautomer thereof, a stereoisomer thereof, or a mixture thereof, wherein:

$R_1$ and $R_2$ are each independently an optionally substituted aryl;

$R_3$ is selected from the group consisting of —OH, —OCH$_3$, —NH$_2$, and —N(CH$_3$)$_2$;

$R_4$ is a halogen or

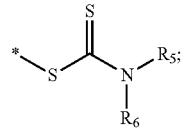

and n is an integer in a range of 1-3, wherein $R_5$ and $R_6$ are each independently selected from the group consisting of a hydrogen, an optionally substituted alkyl, an optionally substituted cycloalkyl, an optionally substituted arylalkyl, and an optionally substituted aryl.

2. The gold(I) complex of formula (I) of claim 1, wherein $R_1$ and $R_2$ are each independently an optionally substituted phenyl.

3. The gold(I) complex of formula (I) of claim 1, wherein $R_1$ and $R_2$ are each phenyl.

4. The gold(I) complex of formula (I) of claim 1, wherein $R_3$ is —NH$_2$.

5. The gold(I) complex of formula (I) of claim 1, wherein n is 1.

6. The gold(I) complex of formula (I) of claim 1, wherein $R_4$ is chloro.

7. The gold(I) complex of formula (I) of claim 1, wherein $R_4$ is

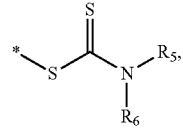

and wherein $R_5$ and $R_6$ are each independently a $C_1$ to $C_8$ alkyl or a $C_7$ to $C_{12}$ arylalkyl.

8. The gold(I) complex of formula (I) of claim 7, wherein $R_5$ and $R_6$ are each methyl, ethyl, or benzyl.

9. The gold(I) complex of formula (I) of claim 1, which is selected from the group consisting of:

10. The gold(I) complex of formula (I) of claim 1, which is selected from the group consisting of:

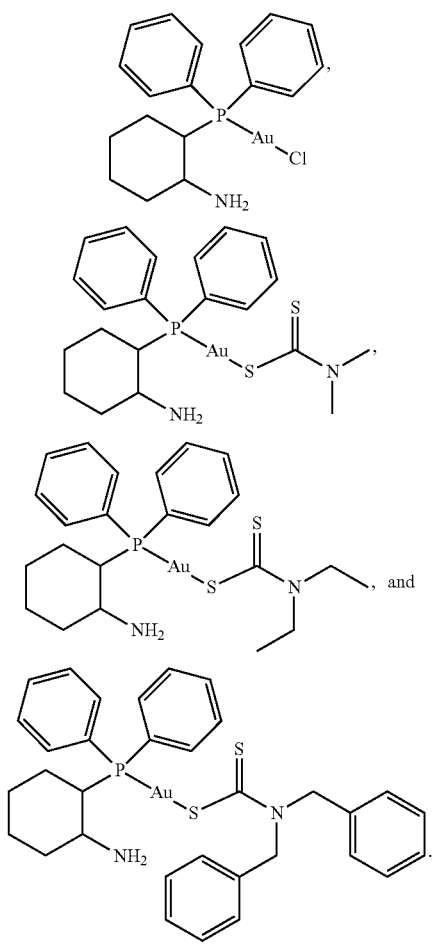

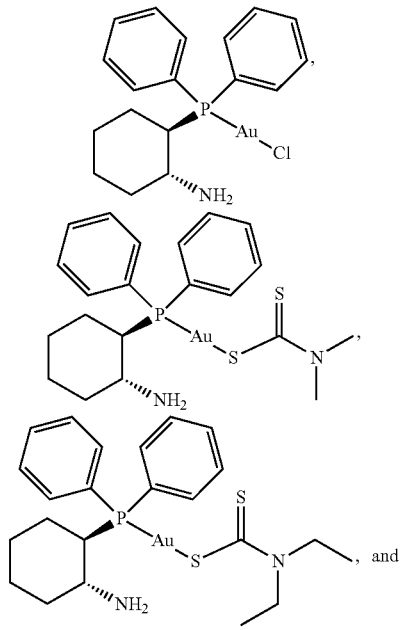

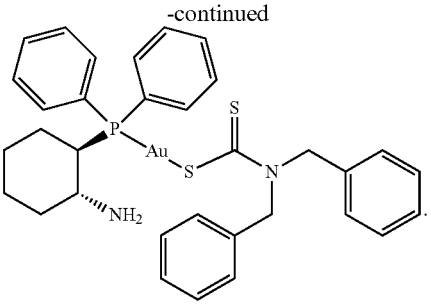

11. A pharmaceutical composition, comprising:
the gold(I) complex of formula (I) of claim 1; and
a pharmaceutically acceptable carrier and/or excipient.

12. The pharmaceutical composition of claim 11, which comprises 0.5-50 µM of the gold(I) complex of formula (I) relative to a total volume of the pharmaceutical composition.

13. The pharmaceutical composition of claim 11, wherein the pharmaceutically acceptable carrier and/or excipient is at least one selected from the group consisting of a buffer, an inorganic salt, a fatty acid, a vegetable oil, a synthetic fatty ester, a surfactant, and a polymer.

14. The pharmaceutical composition of claim 11, wherein the gold(I) complex of formula (I) is selected from the group consisting of:

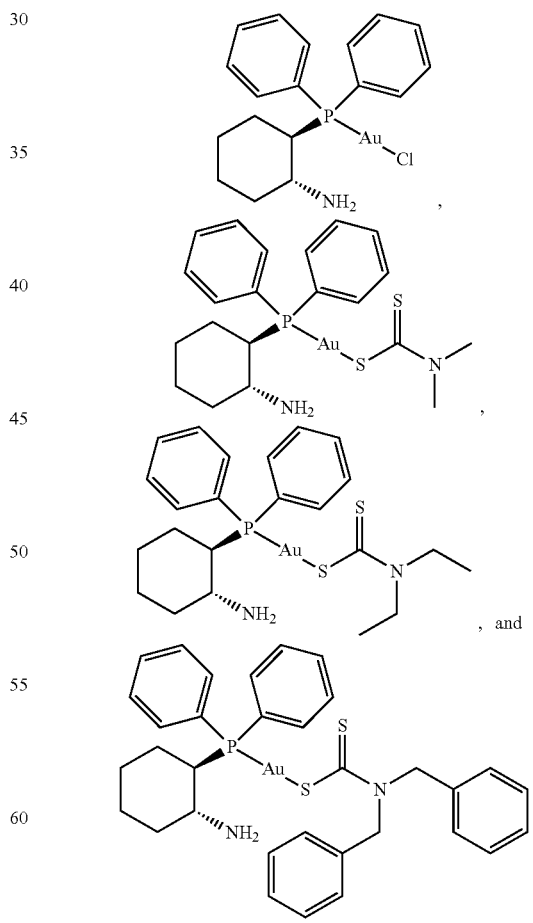

15. A method for treating a proliferative disorder, the method comprising:

administering the pharmaceutical composition of claim 11 to a subject in need of therapy.

16. The method of claim 15, wherein 0.01-50 mg/kg of the gold(I) complex of formula (I) is administered per body weight of the subject.

17. The method of claim 15, wherein the proliferative disorder is cancer.

18. The method of claim 17, wherein the cancer is at least one selected from the group consisting of lung cancer, cervical cancer, and liver cancer.

19. The method of claim 17, wherein the cancer is resistant to at least one platinum-based chemotherapy drug.

20. The method of claim 19, wherein the platinum-based chemotherapy drug is cisplatin.

\* \* \* \* \*